(12) United States Patent
Tsien et al.

(10) Patent No.: US 7,060,793 B2
(45) Date of Patent: Jun. 13, 2006

(54) CIRCULARLY PERMUTED FLUORESCENT PROTEIN INDICATORS

(75) Inventors: Roger Y. Tsien, La Jolla, CA (US); Geoffrey Baird, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 556 days.

(21) Appl. No.: 09/999,745

(22) Filed: Oct. 23, 2001

(65) Prior Publication Data

US 2002/0157120 A1    Oct. 24, 2002

Related U.S. Application Data

(63) Continuation-in-part of application No. 09/316,920, filed as application No. PCT/US00/13684 on May 17, 2000, now Pat. No. 6,699,687.

(51) Int. Cl.
C07K 14/00 (2006.01)
C07K 1/00 (2006.01)
C12N 15/00 (2006.01)
C12N 15/12 (2006.01)
C12N 15/63 (2006.01)

(52) U.S. Cl. .................... 530/350; 530/402; 435/69.7; 435/320.1; 435/325

(58) Field of Classification Search ............... 530/350, 530/402; 435/69.7, 320.1, 325
See application file for complete search history.

(56) References Cited

U.S. PATENT DOCUMENTS 4,603,209 A  7/1986  Tsien et al. .................. 548/236
5,049,673 A  9/1991  Tsien et al. .................. 548/107
5,439,797 A  8/1995  Tsien et al. .................. 435/7.21
5,958,713 A  9/1999  Thastrup et al. ............ 435/69.1

OTHER PUBLICATIONS

Graf et al. Random circular permutation. Proc. Natl. Acad. Sci. USA. 93:11591-11596 (1996).*
Mickle JE et al. Genotype-phenotype relationships in cystic fibrosis. Med Clin North Am. 2000 May;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Abedi et al., "Genetic insertion of peptides into pre-selected regions of GFP"*Nucl. Acids Res.* 26:623-630 (1998).
Graf et al., "Random circular permutation" *Proc. Natl. Acad.* 93:11591-11596 (1996).
Miyawaki et al., "Fluorescent indicators for $Ca^{2+}$ based on green fluorescent proteins and calmodulin" *Nature* 388:882-887 (1997).
Romoser et al., "Detection in Living Cells of $Ca^{2+}$-dependent Changes in Fluorescent Emission of an Indicator Composed of Two Green Fluorescent Protein Variants Linked by a Calmodulin-binding Sequence" *The Journal of Biological Chemistry* 272(2)):13270-13274 (1997).
Topell et al., "Circularly permuted variants of the green fluorescent protein" *FEBS Letters;* 457: 283-289 (1999).
Heikal et al., "Molecular spectroscopy and dynamics of intrinsically fluorescent proteins: Coral red (dsRed) and yellow (citrine)" *Proc. Natl. Acad. Sci. USA* 97(22): 11996-12001 (2001).

* cited by examiner

*Primary Examiner*—Joseph Murphy
(74) *Attorney, Agent, or Firm*—Townsend and Townsend and Crew LLP

(57) ABSTRACT

Polynucleotides encoding fluorescent indicators, which contain a sensor polypeptide inserted within a fluorescent moiety, are provided, as are polypeptides encoded by such polynucleotides. Also provided are circularly permuted fluorescent polypeptides and polynucleotides encoding the circularly permuted fluorescent polypeptides. In addition, methods of using the fluorescent indicators and the circularly permuted fluorescent polypeptides are provided.

13 Claims, 14 Drawing Sheets

YFP, Calmodulin Insertion Sequence Summary

MVSKGEE.......LEYN GGTMHDQLT....... QMMTAKEL NSHNVY......MDELYK

YFP Nter | YFP | Cam Nter | Cam Cter | YFP | YFP Cter
Linker | | | Linker

YFP, Zif Insertion Sequence Summary

MVSKGEE.......LEYN GGTRPYACPVESCDRRFSRSDELTRHIRIHTEL NSHNVY......MDELYK

YFP Nter | YFP | Zif Nter | Zif Cter | YFP | YFP Cter
Linker | | | Linker

*FIG. 1*

SVQST Calmodulin Fusion Titrations

Random Circular Permutation 2

- Digest With DNAse, Mn
- Repair Nicks, Blunt Ends
- Clone into Blunt Expression Vector
  (3 Out-of-Frame Stop Codons)

Insertions Into GFP

- Insertions into GFP Are Topologically Similiar ti Insertions of cpGFP into Protein of Choice

- GFP Insertions Are Known to be Sensors

SEQUENCE LISTING

```
<160> NUMBER OF SEQ ID NOS: 67

<210> SEQ ID NO 1
<211> LENGTH: 6
<212> TYPE: PRT
<213> ORGANISM: Artificial Sequence
<220> FEATURE:
<223> OTHER INFORMATION: Linker moiety

<400> SEQUENCE: 1
```

```
Gly Gly Thr Gly Glu Leu
 1               5
```

<210> SEQ ID NO 2
<211> LENGTH: 6
<212> TYPE: PRT
<213> ORGANISM: Artificial Sequence
<220> FEATURE:
<223> OTHER INFORMATION: Linker moiety

<400> SEQUENCE: 2

```
Phe Lys Thr Arg His Asn
 1               5
```

<210> SEQ ID NO 3
<211> LENGTH: 238
<212> TYPE: PRT
<213> ORGANISM: Aequorea victoria

<400> SEQUENCE: 3

```
Met Ser Lys Gly Glu Glu Leu Phe Thr Gly Val Val Pro Ile Leu Val
 1               5                  10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Gly Ile Thr His Gly Met Asp Glu Leu Tyr Lys
225                 230                 235
```

<210> SEQ ID NO 4
<211> LENGTH: 239
<212> TYPE: PRT
<213> ORGANISM: Aequorea victoria

<400> SEQUENCE: 4

```
Met Val Ser Lys Gly Glu Glu Leu Phe Thr Gly Val Val Pro Ile Leu
 1               5                  10                  15
```

-continued

Val Glu Leu Asp Gly Asp Val Asn Gly His Lys Phe Ser Val Ser Gly
        20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 5
<211> LENGTH: 239
<212> TYPE: PRT
<213> ORGANISM: Aequorea victoria

<400> SEQUENCE: 5

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
        20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn

```
                145                 150                 155                 160
Gly Ile Lys Val Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 6
<211> LENGTH: 239
<212> TYPE: PRT
<213> ORGANISM: Aequorea victoria

<400> SEQUENCE: 6

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 7
<211> LENGTH: 239
<212> TYPE: PRT
<213> ORGANISM: Aequorea victoria

<400> SEQUENCE: 7

Met Val Ser Lys Gly Glu Glu Leu Phe Thr Gly Val Val Pro Ile Leu
```

```
                1               5                  10                 15
Val Glu Leu Asp Gly Asp Val Asn Gly His Arg Phe Ser Val Ser Gly
                20                 25                 30

Glu Gly Glu Gly Asp Ala Thr Tyr Gly Lys Leu Thr Leu Lys Phe Ile
                35                 40                 45

Cys Thr Thr Gly Lys Leu Pro Val Pro Trp Pro Thr Leu Val Thr Thr
                50                 55                 60

Leu Thr Trp Gly Val Gln Cys Phe Ser Arg Tyr Pro Asp His Met Lys
65                      70                 75                 80

Gln His Asp Phe Phe Lys Ser Ala Met Pro Glu Gly Tyr Val Gln Glu
                85                 90                 95

Arg Thr Ile Phe Phe Lys Asp Asp Gly Asn Tyr Lys Thr Arg Ala Glu
                100                105                110

Val Lys Phe Glu Gly Asp Thr Leu Val Asn Arg Ile Glu Leu Lys Gly
                115                120                125

Ile Asp Phe Lys Glu Asp Gly Asn Ile Leu Gly His Lys Leu Glu Tyr
                130                135                140

Asn Tyr Ile Ser His Asn Val Tyr Ile Thr Ala Asp Lys Gln Lys Asn
145                     150                155                 160

Gly Ile Lys Ala His Phe Lys Ile Arg His Asn Ile Glu Asp Gly Ser
                165                170                175

Val Gln Leu Ala Asp His Tyr Gln Gln Asn Thr Pro Ile Gly Asp Gly
                180                185                190

Pro Val Leu Leu Pro Asp Asn His Tyr Leu Ser Thr Gln Ser Ala Leu
                195                200                205

Ser Lys Asp Pro Asn Glu Lys Arg Asp His Met Val Leu Leu Glu Phe
                210                215                220

Val Thr Ala Ala Gly Ile Thr Leu Gly Met Asp Glu Leu Tyr Lys
225                     230                235

<210> SEQ ID NO 8
<211> LENGTH: 238
<212> TYPE: PRT
<213> ORGANISM: Aequorea victoria

<400> SEQUENCE: 8

Met Ser Lys Gly Glu Glu Leu Phe Thr Gly Val Val Pro Ile Leu Val
1               5                  10                 15

Glu Leu Asp Gly Asp Val Asn Gly His Lys Phe Ser Val Ser Gly Glu
                20                 25                 30

Gly Glu Gly Asp Ala Thr Tyr Gly Lys Leu Thr Leu Lys Phe Ile Cys
                35                 40                 45

Thr Thr Gly Lys Leu Pro Val Pro Trp Pro Thr Leu Val Thr Thr Phe
                50                 55                 60

Gly Tyr Gly Leu Gln Cys Phe Ala Arg Tyr Pro Asp His Met Lys Arg
65                      70                 75                 80

His Asp Phe Phe Lys Ser Ala Met Pro Glu Gly Tyr Val Gln Glu Arg
                85                 90                 95

Thr Ile Phe Phe Lys Asp Asp Gly Asn Tyr Lys Thr Arg Ala Glu Val
                100                105                110

Lys Phe Glu Gly Asp Thr Leu Val Asn Arg Ile Glu Leu Lys Gly Ile
                115                120                125

Asp Phe Lys Glu Asp Gly Asn Ile Leu Gly His Lys Leu Glu Tyr Asn
                130                135                140
```

```
Tyr Asn Ser Gly Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 9
<211> LENGTH: 238
<212> TYPE: PRT
<213> ORGANISM: Aequorea victoria

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser Gln Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 10
<211> LENGTH: 239
<212> TYPE: PRT
<213> ORGANISM: Aequorea victoria

<400> SEQUENCE: 10
```

-continued

```
Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                      55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser Gly Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 11
<211> LENGTH: 239
<212> TYPE: PRT
<213> ORGANISM: Aequorea victoria

<400> SEQUENCE: 11

```
Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                      55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140
```

Asn Tyr Asn Ser Gln Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 12
<211> LENGTH: 720
<212> TYPE: DNA
<213> ORGANISM: Aequorea victoria

<400> SEQUENCE: 12

| | | |
|---|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 13
<211> LENGTH: 720
<212> TYPE: DNA
<213> ORGANISM: Aequorea victoria

<400> SEQUENCE: 13

| | | |
|---|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcgtgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |

| tacctgagct accagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 14
<211> LENGTH: 720
<212> TYPE: DNA
<213> ORGANISM: Aequorea victoria

<400> SEQUENCE: 14

| atggtgagca agggcgagga gctgttcacc ggggtggtgc ccatcctggt cgagctggac | 60 |
| ggcgacgtaa acggccacag gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgacctg ggcgtgcag tgcttcagcc gctaccccga ccacatgaag | 240 |
| cagcacgact tcttcaagtc cgccatgccc gaaggctacg tccaggagcg taccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacat cagccacaac gtctatatca ccgccgacaa gcagaagaac | 480 |
| ggcatcaagg cccacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 15
<211> LENGTH: 720
<212> TYPE: DNA
<213> ORGANISM: Aequorea victoria

<400> SEQUENCE: 15

| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgaag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 16
<211> LENGTH: 714
<212> TYPE: DNA
<213> ORGANISM: Aequorea victoria

<400> SEQUENCE: 16

| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |

-continued

| | | |
|---|---|---|
| aaacttaccc ttaaatttat ttgcactact ggaaaactac ctgttccatg gccaacactt | 180 |
| gtcactactt tcggttatgg tcttcaatgc tttgcaagat acccagatca tatgaaacgg | 240 |
| catgactttt tcaagagtgc catgcccgaa ggttatgttc aggaaagaac tatattttc | 300 |
| aaagatgacg ggaactacaa gacacgtgct gaagtcaagt ttgaaggtga tacccttgtt | 360 |
| aatagaatcg agttaaaagg tattgatttt aaagaagatg gaaacattct tggacacaaa | 420 |
| ttggaataca actataactc aggcaatgta tacatcatgg cagacaaaca aaagaatgga | 480 |
| atcaaagtta acttcaaaat tagacacaac attgaagatg gaagcgttca actagcagac | 540 |
| cattatcaac aaaatactcc aattggcgat ggccctgtcc ttttaccaga caaccattac | 600 |
| ctgtcctatc aatctgccct ttcgaaagat cccaacgaaa agagagacca catggtcctt | 660 |
| cttgagtttg taacagctgc tgggattaca catggcatgg atgaactata caaa | 714 |

<210> SEQ ID NO 17
<211> LENGTH: 714
<212> TYPE: DNA
<213> ORGANISM: Aequorea victoria

<400> SEQUENCE: 17

| | | |
|---|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tcggttatgg tcttcaatgc tttgcaagat acccagatca tatgaaacgg | 240 |
| catgactttt tcaagagtgc catgcccgaa ggttatgttc aggaaagaac tatattttc | 300 |
| aaagatgacg ggaactacaa gacacgtgct gaagtcaagt ttgaaggtga tacccttgtt | 360 |
| aatagaatcg agttaaaagg tattgatttt aaagaagatg gaaacattct tggacacaaa | 420 |
| ttggaataca actataactc aggcaatgta tacatcatgg cagacaaaca aaagaatgga | 480 |
| atcaaagtta acttcaaaat tagacacaac attgaagatg gaagcgttca actagcagac | 540 |
| cattatcaac aaaatactcc aattggcgat ggccctgtcc ttttaccaga caaccattac | 600 |
| ctgtcctatc aatctgccct ttcgaaagat cccaacgaaa agagagacca catggtcctt | 660 |
| cttgagtttg taacagctgc tgggattaca catggcatgg atgaactata caaa | 714 |

<210> SEQ ID NO 18
<211> LENGTH: 720
<212> TYPE: DNA
<213> ORGANISM: Aequorea victoria

<400> SEQUENCE: 18

| | | |
|---|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcgtgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccgcaac gtctatatca tggccgacaa gcagaagaac | 480 |
| ggcatcaagg tgaacttcaa gatccgccac aacatcgagg acggcagcgt gcagctcgcc | 540 |

```
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720
```

```
<210> SEQ ID NO 19
<211> LENGTH: 720
<212> TYPE: DNA
<213> ORGANISM: Aequorea victoria

<400> SEQUENCE: 19
```

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcgtgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccagaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720
```

```
<210> SEQ ID NO 20
<211> LENGTH: 5
<212> TYPE: PRT
<213> ORGANISM: Homo sapiens

<400> SEQUENCE: 20
```

Lys Lys Lys Arg Lys
1               5

```
<210> SEQ ID NO 21
<211> LENGTH: 26
<212> TYPE: PRT
<213> ORGANISM: Homo sapiens

<400> SEQUENCE: 21
```

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

```
<210> SEQ ID NO 22
<211> LENGTH: 4
<212> TYPE: PRT
<213> ORGANISM: Homo sapiens

<400> SEQUENCE: 22
```

Lys Asp Glu Leu
1

```
<210> SEQ ID NO 23
<211> LENGTH: 4
<212> TYPE: PRT
<213> ORGANISM: Homo sapiens
```

```
<220> FEATURE:
<221> NAME/KEY: VARIANT
<222> LOCATION: (1)...(4)
<223> OTHER INFORMATION: Xaa = Any Amino Acid

<400> SEQUENCE: 23

Cys Ala Ala Xaa
1

<210> SEQ ID NO 24
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 24

Cys Cys Xaa Xaa
1

<210> SEQ ID NO 25
<211> LENGTH: 26
<212> TYPE: PRT
<213> ORGANISM: Oryctolagus cuniculus

<400> SEQUENCE: 25

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 26
<211> LENGTH: 20
<212> TYPE: PRT
<213> ORGANISM: Meleagris gallopavo

<400> SEQUENCE: 26

Ala Arg Arg Lys Trp Gln Lys Thr Gly His Ala Val Arg Ala Ile Gly
1               5                   10                  15

Arg Leu Ser Ser
            20

<210> SEQ ID NO 27
<211> LENGTH: 20
<212> TYPE: PRT
<213> ORGANISM: Rattus norvegicus

<400> SEQUENCE: 27

Ala Arg Arg Lys Leu Lys Gly Ala Ile Leu Thr Thr Met Leu Ala Thr
1               5                   10                  15

Arg Asn Phe Ser
            20

<210> SEQ ID NO 28
<211> LENGTH: 17
<212> TYPE: PRT
<213> ORGANISM: Gallus gallus

<400> SEQUENCE: 28

Gly Val Arg Asn Ile Lys Ser Met Trp Glu Lys Gly Asn Val Phe Ser
1               5                   10                  15

Ser
```

```
<210> SEQ ID NO 29
<211> LENGTH: 20
<212> TYPE: PRT
<213> ORGANISM: Rattus norvegicus

<400> SEQUENCE: 29

Ala Arg Arg Lys Leu Lys Ala Ala Val Lys Ala Val Val Ala Ser Ser
 1               5                  10                  15

Arg Leu Gly Ser
            20

<210> SEQ ID NO 30
<211> LENGTH: 26
<212> TYPE: PRT
<213> ORGANISM: Oryctolagus cuniculus

<400> SEQUENCE: 30

Phe Met Asn Asn Trp Glu Val Tyr Lys Leu Leu Ala His Ile Arg Pro
 1               5                  10                  15

Pro Ala Pro Lys Ser Gly Ser Tyr Thr Val
            20                  25

<210> SEQ ID NO 31
<211> LENGTH: 24
<212> TYPE: PRT
<213> ORGANISM: Bos taurus

<400> SEQUENCE: 31

Ala Arg Lys Glu Val Ile Arg Asn Lys Ile Arg Ala Ile Gly Lys Met
 1               5                  10                  15

Ala Arg Val Phe Ser Val Leu Arg
            20

<210> SEQ ID NO 32
<211> LENGTH: 26
<212> TYPE: PRT
<213> ORGANISM: Oryctolagus cuniculus

<400> SEQUENCE: 32

Leu Arg Arg Leu Ile Asp Ala Tyr Ala Phe Arg Ile Tyr Gly His Trp
 1               5                  10                  15

Val Lys Lys Gly Gln Gln Gln Asn Arg Gly
            20                  25

<210> SEQ ID NO 33
<211> LENGTH: 27
<212> TYPE: PRT
<213> ORGANISM: Oryctolagus cuniculus

<400> SEQUENCE: 33

Arg Gly Lys Phe Lys Val Ile Cys Leu Thr Val Leu Ala Ser Val Arg
 1               5                  10                  15

Ile Tyr Tyr Gln Tyr Arg Arg Val Lys Pro Gly
            20                  25

<210> SEQ ID NO 34
<211> LENGTH: 28
<212> TYPE: PRT
<213> ORGANISM: Homo sapiens

<400> SEQUENCE: 34
```

-continued

Leu Arg Arg Gly Gln Ile Leu Trp Phe Arg Gly Leu Asn Arg Ile Gln
1               5                   10                  15

Thr Gln Ile Lys Val Val Asn Ala Phe Ser Ser Ser
                20                  25

<210> SEQ ID NO 35
<211> LENGTH: 21
<212> TYPE: PRT
<213> ORGANISM: Bos taurus

<400> SEQUENCE: 35

Arg Arg Lys His Leu Gln Arg Pro Ile Phe Arg Leu Arg Cys Leu Val
1               5                   10                  15

Lys Gln Leu Glu Lys
                20

<210> SEQ ID NO 36
<211> LENGTH: 21
<212> TYPE: PRT
<213> ORGANISM: Bos taurus

<400> SEQUENCE: 36

Thr Glu Lys Met Trp Gln Arg Leu Lys Gly Ile Leu Arg Cys Leu Val
1               5                   10                  15

Lys Gln Leu Glu Lys
                20

<210> SEQ ID NO 37
<211> LENGTH: 23
<212> TYPE: PRT
<213> ORGANISM: Rattus norvegicus

<400> SEQUENCE: 37

Lys Arg Arg Ala Ile Gly Phe Lys Lys Leu Ala Glu Ala Val Lys Phe
1               5                   10                  15

Ser Ala Lys Leu Met Gly Gln
                20

<210> SEQ ID NO 38
<211> LENGTH: 28
<212> TYPE: PRT
<213> ORGANISM: Bos taurus

<400> SEQUENCE: 38

Ile Lys Pro Ala Lys Arg Met Lys Phe Lys Thr Val Cys Tyr Leu Leu
1               5                   10                  15

Val Gln Leu Met His Cys Arg Lys Met Phe Lys Ala
                20                  25

<210> SEQ ID NO 39
<211> LENGTH: 20
<212> TYPE: PRT
<213> ORGANISM: Bordetella pertussin

<400> SEQUENCE: 39

Ile Asp Leu Leu Trp Lys Ile Ala Arg Ala Gly Ala Arg Ser Ala Val
1               5                   10                  15

Gly Thr Glu Ala
                20

<210> SEQ ID NO 40
<211> LENGTH: 27

```
<212> TYPE: PRT
<213> ORGANISM: Homo sapiens

<400> SEQUENCE: 40

Lys Ala His Lys Ala Ala Thr Lys Ile Gln Ala Ser Phe Arg Gly His
 1               5                  10                  15

Ile Thr Arg Lys Lys Leu Lys Gly Glu Lys Lys
                20                  25

<210> SEQ ID NO 41
<211> LENGTH: 24
<212> TYPE: PRT
<213> ORGANISM: Homo sapiens

<400> SEQUENCE: 41

Lys Thr Ala Ser Pro Trp Lys Ser Ala Arg Leu Met Val His Thr Val
 1               5                  10                  15

Ala Thr Phe Asn Ser Ile Lys Glu
                20

<210> SEQ ID NO 42
<211> LENGTH: 25
<212> TYPE: PRT
<213> ORGANISM: Rattus norvegicus

<400> SEQUENCE: 42

Lys Lys Lys Lys Lys Arg Phe Ser Phe Lys Lys Ser Phe Lys Leu Ser
 1               5                  10                  15

Gly Phe Ser Phe Lys Lys Ser Lys Lys
                20                  25

<210> SEQ ID NO 43
<211> LENGTH: 24
<212> TYPE: PRT
<213> ORGANISM: Mus musculus

<400> SEQUENCE: 43

Lys Lys Lys Lys Lys Phe Ser Phe Lys Lys Pro Phe Lys Leu Ser Gly
 1               5                  10                  15

Leu Ser Phe Lys Arg Asn Arg Lys
                20

<210> SEQ ID NO 44
<211> LENGTH: 31
<212> TYPE: PRT
<213> ORGANISM: Homo sapiens

<400> SEQUENCE: 44

Lys Gln Gln Lys Glu Lys Thr Arg Trp Leu Asn Thr Pro Asn Thr Tyr
 1               5                  10                  15

Leu Arg Val Asn Val Ala Asp Glu Val Gln Arg Asn Met Gly Ser
                20                  25                  30

<210> SEQ ID NO 45
<211> LENGTH: 21
<212> TYPE: PRT
<213> ORGANISM: Mus musculus

<400> SEQUENCE: 45

Lys Asp Gln Val Ala Asn Ser Ala Phe Gln Glu Arg Leu Arg Lys His
 1               5                  10                  15

Gly Leu Glu Val Ile
```

-continued

<210> SEQ ID NO 46
<211> LENGTH: 21
<212> TYPE: PRT
<213> ORGANISM: Human immunodeficiency virus type 1

<400> SEQUENCE: 46

Tyr His Arg Leu Arg Asp Leu Leu Ile Val Lys Arg Ile Val Glu
1               5                   10                  15

Leu Leu Gly Arg Arg
            20

<210> SEQ ID NO 47
<211> LENGTH: 23
<212> TYPE: PRT
<213> ORGANISM: Bos taurus

<400> SEQUENCE: 47

Gln Gln Leu Ala Thr Leu Ile Gln Lys Thr Tyr Arg Gly Trp Arg Cys
1               5                   10                  15

Arg Thr His Tyr Gln Leu Met
            20

<210> SEQ ID NO 48
<211> LENGTH: 24
<212> TYPE: PRT
<213> ORGANISM: Mus musculus

<400> SEQUENCE: 48

Arg Ala Ala Cys Ile Arg Ile Gln Lys Thr Ile Arg Gly Trp Leu Leu
1               5                   10                  15

Arg Lys Arg Tyr Leu Cys Met Gln
            20

<210> SEQ ID NO 49
<211> LENGTH: 14
<212> TYPE: PRT
<213> ORGANISM: Vespa crabro

<400> SEQUENCE: 49

Ile Asn Leu Lys Ala Leu Ala Ala Leu Ala Lys Lys Ile Leu
1               5                   10

<210> SEQ ID NO 50
<211> LENGTH: 26
<212> TYPE: PRT
<213> ORGANISM: Apis mellifera

<400> SEQUENCE: 50

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 51
<211> LENGTH: 30
<212> TYPE: PRT
<213> ORGANISM: Bos taurus

<400> SEQUENCE: 51

His Ser Gln Gly Thr Phe Thr Ser Asp Tyr Ser Lys Tyr Leu Asp
1               5                   10                  15

```
Ser Arg Arg Ala Gln Asp Phe Val Gln Trp Leu Met Asn Thr
        20                  25                  30

<210> SEQ ID NO 52
<211> LENGTH: 27
<212> TYPE: PRT
<213> ORGANISM: Sus scrofa

<400> SEQUENCE: 52

His Ser Asp Gly Thr Phe Thr Ser Glu Leu Ser Arg Leu Arg Asp Ser
 1               5                  10                  15

Ala Arg Leu Gln Arg Leu Leu Gln Gly Leu Val
            20                  25

<210> SEQ ID NO 53
<211> LENGTH: 28
<212> TYPE: PRT
<213> ORGANISM: Homo sapiens

<400> SEQUENCE: 53

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 54
<211> LENGTH: 33
<212> TYPE: PRT
<213> ORGANISM: Sus scrofa

<400> SEQUENCE: 54

Tyr Ala Asp Gly Thr Phe Ile Ser Asp Tyr Ser Ala Ile Met Asn Lys
 1               5                  10                  15

Ile Arg Gln Gln Asp Phe Val Asn Trp Leu Leu Ala Gln Gln Lys
            20                  25                  30

Ser

<210> SEQ ID NO 55
<211> LENGTH: 17
<212> TYPE: PRT
<213> ORGANISM: Artificial Sequence
<220> FEATURE:
<223> OTHER INFORMATION: Calmodulin binding peptide-2

<400> SEQUENCE: 55

Lys Leu Trp Lys Lys Leu Leu Lys Leu Leu Lys Lys Leu Leu Lys Leu
 1               5                  10                  15

Gly

<210> SEQ ID NO 56
<211> LENGTH: 5
<212> TYPE: PRT
<213> ORGANISM: Artificial Sequence
<220> FEATURE:
<223> OTHER INFORMATION: Linker moiety; sequence repeated indefinitely

<400> SEQUENCE: 56

Gly Gly Gly Gly Ser
     1               5

<210> SEQ ID NO 57
<211> LENGTH: 12
```

```
<212> TYPE: PRT
<213> ORGANISM: Artificial Sequence
<220> FEATURE:
<223> OTHER INFORMATION: Linker moiety

<400> SEQUENCE: 57

Gly Lys Ser Ser Gly Ser Gly Ser Glu Ser Lys Ser
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Linker moiety

<400> SEQUENCE: 58

Gly Ser Thr Ser Gly Ser Gly Lys Ser Ser Glu Gly Lys Gly
1               5                   10

<210> SEQ ID NO 59
<211> LENGTH: 18
<212> TYPE: PRT
<213> ORGANISM: Artificial Sequence
<220> FEATURE:
<223> OTHER INFORMATION: Linker moiety

<400> SEQUENCE: 59

Gly Ser Thr Ser Gly Ser Gly Lys Ser Ser Glu Gly Ser Gly Ser Thr
1               5                   10                  15

Lys Gly

<210> SEQ ID NO 60
<211> LENGTH: 14
<212> TYPE: PRT
<213> ORGANISM: Artificial Sequence
<220> FEATURE:
<223> OTHER INFORMATION: Linker moiety

<400> SEQUENCE: 60

Gly Ser Thr Ser Gly Ser Gly Lys Ser Ser Glu Gly Lys Gly
1               5                   10

<210> SEQ ID NO 61
<211> LENGTH: 18
<212> TYPE: PRT
<213> ORGANISM: Artificial Sequence
<220> FEATURE:
<223> OTHER INFORMATION: Linker moiety

<400> SEQUENCE: 61

Gly Ser Thr Ser Gly Ser Gly Lys Pro Gly Ser Gly Glu Gly Ser Thr
1               5                   10                  15

Lys Gly

<210> SEQ ID NO 62
<211> LENGTH: 14
<212> TYPE: PRT
<213> ORGANISM: Artificial Sequence
<220> FEATURE:
<223> OTHER INFORMATION: Linker moiety

<400> SEQUENCE: 62

Glu Gly Lys Ser Ser Gly Ser Gly Ser Glu Ser Lys Glu Phe
1               5                   10
```

<210> SEQ ID NO 63
<211> LENGTH: 6
<212> TYPE: PRT
<213> ORGANISM: Artificial Sequence
<220> FEATURE:
<223> OTHER INFORMATION: Linker moiety

<400> SEQUENCE: 63

Gly Gly Thr Gly Gly Ser
 1               5

<210> SEQ ID NO 64
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 64

```
atg gtg agc aag ggc gag gag ctg ttc acc ggg gtg gtg ccc atc ctg        48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc        96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc       144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
    50                  55                  60 ttc ggc tac ggc ctg atg tgc ttc gcc cgc tac ccc gac cac atg aag       240
Phe Gly Tyr Gly Leu Met Cys Phe Ala Arg Tyr Pro Asp His Met Lys
65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac       480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc       528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg       624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
    210                 215                 220
```

```
gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235

<210> SEQ ID NO 65
<211> LENGTH: 239
<212> TYPE: PRT
<213> ORGANISM: Aequorea victoria

<400> SEQUENCE: 65

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 66
<211> LENGTH: 859
<212> TYPE: DNA
<213> ORGANISM: Discosoma sp.
<220> FEATURE:
<221> NAME/KEY: CDS
<222> LOCATION: (54)..(731)

<400> SEQUENCE: 66
gtttcagcca gtgacggtca gtgacagggt gagccacttg gtataccaac aaa atg      56
                                                            Met
                                                            1 agg tct tcc aag aat gtt atc aag gag ttc atg agg ttt aag gtt cgc    104
Arg Ser Ser Lys Asn Val Ile Lys Glu Phe Met Arg Phe Lys Val Arg
        5                   10                  15 atg gaa gga acg gtc aat ggg cac gag ttt gaa ata gaa ggc gaa gga    152
Met Glu Gly Thr Val Asn Gly His Glu Phe Glu Ile Glu Gly Glu Gly
```

-continued

```
                20                  25                  30
gag ggg agg cca tac gaa ggc cac aat acc gta aag ctt aag gta acc      200
Glu Gly Arg Pro Tyr Glu Gly His Asn Thr Val Lys Leu Lys Val Thr
 35                  40                  45 aag ggg gga cct ttg cca ttt gct tgg gat att ttg tca cca caa ttt      248
Lys Gly Gly Pro Leu Pro Phe Ala Trp Asp Ile Leu Ser Pro Gln Phe
 50                  55                  60                  65 cag tat gga agc aag gta tat gtc aag cac cct gcc gac ata cca gac      296
Gln Tyr Gly Ser Lys Val Tyr Val Lys His Pro Ala Asp Ile Pro Asp
                 70                  75                  80 tat aaa aag ctg tca ttt cct gaa gga ttt aaa tgg gaa agg gtc atg      344
Tyr Lys Lys Leu Ser Phe Pro Glu Gly Phe Lys Trp Glu Arg Val Met
             85                  90                  95 aac ttt gaa gac ggt ggc gtc gtt act gta acc cag gat tcc agt ttg      392
Asn Phe Glu Asp Gly Gly Val Val Thr Val Thr Gln Asp Ser Ser Leu
        100                 105                 110 cag gat ggc tgt ttc atc tac aag gtc aag ttc att ggc gtg aac ttt      440
Gln Asp Gly Cys Phe Ile Tyr Lys Val Lys Phe Ile Gly Val Asn Phe
    115                 120                 125 cct tcc gat gga cct gtt atg caa aag aag aca atg ggc tgg gaa gcc      488
Pro Ser Asp Gly Pro Val Met Gln Lys Lys Thr Met Gly Trp Glu Ala
130                 135                 140                 145 agc act gag cgt ttg tat cct cgt gat ggc gtg ttg aaa gga gag att      536
Ser Thr Glu Arg Leu Tyr Pro Arg Asp Gly Val Leu Lys Gly Glu Ile
                150                 155                 160 cat aag gct ctg aag ctg aaa gac ggt ggt cat tac cta gtt gaa ttc      584
His Lys Ala Leu Lys Leu Lys Asp Gly Gly His Tyr Leu Val Glu Phe
            165                 170                 175 aaa agt att tac atg gca aag aag cct gtg cag cta cca ggg tac tac      632
Lys Ser Ile Tyr Met Ala Lys Lys Pro Val Gln Leu Pro Gly Tyr Tyr
        180                 185                 190 tat gtt gac tcc aaa ctg gat ata aca agc cac aac gaa gac tat aca      680
Tyr Val Asp Ser Lys Leu Asp Ile Thr Ser His Asn Glu Asp Tyr Thr
    195                 200                 205 atc gtt gag cag tat gaa aga acc gag gga cgc cac cat ctg ttc ctt      728
Ile Val Glu Gln Tyr Glu Arg Thr Glu Gly Arg His His Leu Phe Leu
210                 215                 220                 225 taa ggctgaactt ggctcagacg tgggtgagcg gtaatgacca caaaaggcag           781
cgaagaaaaa ccatgatcgt tttttttagg ttggcagcct gaaatcgtag gaaatacatc   841
agaaatgtta caaacagg                                                  859
```

<210> SEQ ID NO 67
<211> LENGTH: 225
<212> TYPE: PRT
<213> ORGANISM: Discosoma sp.

<400> SEQUENCE: 67

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
 65                  70                  75                  80
```

-continued

```
Asp Tyr Lys Lys Leu Ser Phe Pro Glu Gly Phe Lys Trp Glu Arg Val
            85              90                  95

Met Asn Phe Glu Asp Gly Gly Val Val Thr Val Thr Gln Asp Ser Ser
            100             105             110

Leu Gln Asp Gly Cys Phe Ile Tyr Lys Val Lys Phe Ile Gly Val Asn
            115             120             125

Phe Pro Ser Asp Gly Pro Val Met Gln Lys Lys Thr Met Gly Trp Glu
        130             135             140

Ala Ser Thr Glu Arg Leu Tyr Pro Arg Asp Gly Val Leu Lys Gly Glu
145             150             155             160

Ile His Lys Ala Leu Lys Leu Lys Asp Gly Gly His Tyr Leu Val Glu
                165             170             175

Phe Lys Ser Ile Tyr Met Ala Lys Lys Pro Val Gln Leu Pro Gly Tyr
            180             185             190

Tyr Tyr Val Asp Ser Lys Leu Asp Ile Thr Ser His Asn Glu Asp Tyr
        195             200             205

Thr Ile Val Glu Gln Tyr Glu Arg Thr Glu Gly Arg His His Leu Phe
    210             215             220

Leu
225
```

CIRCULARLY PERMUTED FLUORESCENT PROTEIN INDICATORS

This application is a continuation-in-part of U.S. Ser. No. 09/316,920, filed May 21, 1999, now U.S. Pat. No. 6,699,687 the entire contents of which is incorporated herein by reference.

This invention was made with Government support under Grant No. NS27177, awarded by the National Institutes of Health. The Government has certain rights in this invention.

BACKGROUND OF THE INVENTION

1. Field of the Invention

The invention relates generally to fluorescent proteins and more particularly to compositions and methods for measuring the response of a sensor polypeptide to an environmental (e.g., biological, chemical, electrical or physiological) parameter.

2. Background Information

Fluorescent $Ca^{2+}$ indicators such as fara-2, indo-1, fluo-3, and Calcium-Green have been the mainstay of intracellular $Ca^{2+}$ measurement and imaging (see, for example, U.S. Pat. No. 4,603,209 and U.S. Pat. No. 5,049,673). These relatively low molecular weight indicators can suffer from many technical problems relating to ester loading, leakage of the dyes from the cell, compartmentalization in organelles, and perturbation of the indicators by cellular constituents. Although the $Ca^{2+}$-indicating photoprotein aequorin is targetable, the photoresponse to $Ca^{2+}$ is low because it is chemiluminescent. Moreover, aequorins need to incorporate exogenous coelenterazine.

Many effects of $Ca^{2+}$ in cells are mediated by $Ca^{2+}$ binding to calmodulin (CaM), which causes CaM to bind and activate target proteins or peptide sequences. Based on the NMR structure of CaM bound to the 26 residue M13 $Ca^{2+}$-binding peptide of myosin light-chain kinase, Porumb et al. fused the C-terminus of CaM via a Gly-Gly spacer to M13. $Ca^{2+}$ binding switched the resulting hybrid protein (CaM-M13) from a dumbbell-like extended form to a compact globular form similar to the CaM-M13 intermolecular complex (see, Porumb et al., *Prot. Engineering* 7:109–115 (1994)).

Measurement of a binding member concentration in vitro or in vivo by non-invasive techniques can help elucidate the physiological function of the binding member. This can also aid in identifying changes that occur in a cell or organism in response to physiological stimuli. For example, cyclic AMP can be detected by fluorescence resonance energy transfer between separately labeled proteins that associate with each other but are not covalently attached to each other (see, U.S. Pat. No. 5,439,797).

The *Aequorea victoria* Green Fluorescent Protein (GFP) is useful as a marker for gene expression, as a fluorescent tag to aid in visualizing protein trafficking, and as a component of indicator systems that allow fluorescent sensing of small molecules and pH. Currently, the use of GFPs as a biosensor is limited to those systems that use GFP fusion proteins as partners for fluorescence resonance energy transfer (FRET) or those that use the subcellular redistribution of GFP fusion proteins as indicators of substrate concentration or the measurement of pH.

Currently, fluorescent molecules designed to measure interactions of proteins rely on cameleon molecules of tandem GFP constructs. In these constructs, conformational changes occur and alter the FRET between the GFPs such that a ratiometric color change is noted. Such cameleon or FRET-sensitive constructs are large molecules, in which protein conformation influences FRET efficiency of two GFPs of different colors. Although insertions into Green Fluorescent Protein have been attempted (see Abedi et al., *Nucleic Acids Research*, 26(2):623–630 (1998)), such insertions have been made to optimize the presentation of short peptide libraries and not to present binding molecules or sensor polypeptides. Additionally, such insertions have been only short insertions of about six amino acids in length. Until now, however, it has not been possible to make a single GFP molecule fluorescence-sensitive to a substrate other than hydrogen ions. Thus, there currently is a desire for smaller constructs useful in measuring interactions of molecules in vitro and in vivo.

SUMMARY OF THE INVENTION

As disclosed herein, when a sensor polypeptide is inserted into a fluorescent protein such as an *Aequorea*-related fluorescent protein (e.g., Green Fluorescent Protein (GFP), Yellow Fluorescent Protein (YFP), Cyan Fluorescent Protein (CFP), or a derivative or mutant thereof) to form a construct, interaction of the sensor polypeptide with a biological, chemical, electrical or physiological parameter, for example, results in a change in fluorescence of the fluorescent protein. Such constructs are useful in measuring interactions of a sensor polypeptides with environmental stimuli in vitro or in vivo or in measuring particular characteristics of a cell (e.g., redox potential, intracellular ion concentration). These constructs rely on the responsiveness of a sensor polypeptide inserted within a GFP-sensor-related protein itself to influence the actual fluorescence of the fluorophore and not the interaction of tandem fluorescent molecules.

Accordingly, the present invention provides an isolated nucleic acid sequence that encodes a fluorescent indicator or chimeric construct, the indicator having a sensor polypeptide that is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide. The fluorescent protein moiety can be any fluorescent protein, including, for example, an *Aequorea*-related fluorescent protein moiety such as a GFP, CFP or YFP moiety, or a *Discosoma*-related fluorescent protein such as dsRED (SEQ ID NO:67), or a mutant of such a fluorescent protein such as the YFP mutant, citrine (S65G/V68L/Q69M/S72A/T203Y; SEQ ID NO: 65). The sensor polypeptide can be any polypeptide moiety, for example, a moiety that undergoes a conformational change upon interaction with a molecule, oxidation-reduction, or changes in electrical or chemical potential. The indicator can further include a linker moiety, linking the N-terminal and C-terminal amino acids of the sensor polypeptide to the fluorescent protein. The linker can be any moiety that provides for linking of the sensor polypeptide to the fluorescent protein moiety, for example, a nucleic acid that encodes GGTGEL (SEQ ID NO:1) or FKTRHN (SEQ ID NO:2). Two or more linker moieties can be attached to two separate polypeptides, that together form a sensor polypeptide. Additionally, the indicator can have a localization sequence, for localizing the indicator, for example, to a particular organelle of a cell. The sensor polypeptide or linker moiety can be inserted at numerous sites including, for example, one or more amino acids between residues 128–148, residues 155–160, residues 168–176, or residues 227–229 of the fluorescent protein moiety (e.g., GFP). In one embodiment, Y145 is used for insertion of the linker or sensor polypeptide.

The present invention also provides a transgenic non-human animal containing a nucleic acid sequence that encodes a fluorescent indicator or chimeric construct, the indicator having a sensor polypeptide that is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide.

The present invention further provides an expression vector having expression control sequences operatively linked to a nucleic acid sequence encoding a fluorescent indicator, thereby providing an expressible fluorescent indicator. The indicator includes a sensor polypeptide that is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide.

The present invention also provides a host cell transfected with an expression vector having an expression control sequence operatively linked to a sequence coding for the expression of a fluorescent indicator. The host cell can be any host cell capable of transfection and expression of the indicator such as, for example, a prokaryote (e.g., *E. coli*), or a eukaryotic cell such as a yeast cell, a mammalian cell, or the like.

The present invention additionally provides a fluorescent indicator polypeptide, which includes a sensor polypeptide that is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide.

The present invention further provides a fluorescent indicator or chimeric construct, which includes a sensor polypeptide that is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide the responsiveness resulting in protonation or deprotonation of the chromophore of the fluorescent protein moiety.

The present invention also provides a method for detecting the presence of an environmental parameter in a sample, by contacting the sample with a fluorescent indicator or chimeric construct, the fluorescent indicator or chimeric construct including a sensor polypeptide that is responsive to a chemical, biological, electrical, or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide, and detecting a change in fluorescence wherein a change is indicative of the presence of a parameter which affects the sensor polypeptide.

The invention additionally provides an isolated nucleic acid sequence encoding a circularly permuted fluorescent protein and further provides the polypeptide encoded thereby, the polypeptide having a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end, and wherein the amino and carboxy terminal ends of the circularly permuted fluorescent protein moiety are different from the amino-terminal and carboxy-terminal amino acids of the fluorescent protein. The fluorescent protein can be any fluorescent protein as disclosed herein, including a GFP or derivative or mutant thereof such as citrine, or a dsRed protein or mutant thereof.

The invention further provides a vector, including an expression vector, which contains expression control sequences operatively linked to a nucleic acid sequence coding for the expression of a fluorescent indicator, the indicator having a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein. Also provided is a host cell containing such an expression vector.

The invention also provides a method of producing a nucleic acid sequence encoding a fluorescent indicator, by linking a nucleic acid sequence encoding a linker moiety to the 5' nucleotide of a polynucleotide encoding a fluorescent protein, circularizing the polynucleotide with the nucleic acid sequence encoding the linker sequence, and cleaving the circularized polynucleotide with a nuclease, wherein cleavage linearizes the circularized polynucleotide.

The invention further provides a method of producing a circularly permuted fluorescent protein by expressing a nucleic acid sequence encoding a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein.

The present invention provides a circularly permuted fluorescent protein moiety, which includes a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein; and a sensor polypeptide which is response to a chemical, biological, electrical or physiological parameter. In one embodiment, the fluorescent protein of the circularly permuted fluorescent protein moiety is citrine (SEQ ID NO:65). In another embodiment, the fluorescent protein of the circularly permuted fluorescent protein moiety is dsRed (SEQ ID NO:67).

The present invention also provides a method of producing a circularly permuted fluorescent nucleic acid sequence.

Such a method can be performed, for example, by linking a nucleic acid sequence encoding a linker moiety to the 5' nucleotide of a polynucleotide encoding a fluorescent protein; circularizing the polynucleotide with the nucleic acid sequence encoding the linker sequence; and cleaving the circularized polynucleotide with a nuclease, wherein cleavage linearizes the circularized polynucleotide. In one embodiment, the polynucleotide encoding the fluorescent protein is a polynucleotide encoding citrine (SEQ ID NO:64). The method can further comprise expressing the circularly permuted fluorescent nucleic acid sequence. Accordingly, the present invention further provides a circularly permuted fluorescent protein produced by such a method, for example, a circularly permuted fluorescent protein comprising citrine (SEQ ID NO:65).

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1 shows the designs of a calmodulin or a Zif268 insertion into a fluorescent indicator of the present invention.

FIG. 9A shows a normalized one-photon absorption (solid line and points) and emission (open points) spectra of dsRed (●○) and citrine (▲▼△▽), at pH 9. A new absorption band (▼) of citrine appears (412 nm) in pH 4.9 buffer whereas its emission (∇) reveals a broader blue wing of the 524-nm band. The non-normalized 514 nm absorption band of citrine in pH 9 is ≈3.7 times weaker in pH 4.9 before normalization.

FIG. 9B shows the 2P-excitation cross-section of dsRed (●) and citrine (○) over the 730–990 nm, where $GM=10^{-50}$ $cm^4 s/photon$. Note that $\sigma_{2P}$ of dsRed continues to rise at 990 nm.

FIG. 10A shows the excitation intensity dependence of photoconversion kinetics of dsRed (pH 9.0) FCS correlation curves as a function of $k_{ex}$ at 488 nm (≈0.4–7.3 $kW/cm^2$).

FIGS. 10B and 10C show the light-driven fluorescence flicker fraction (FIG. 10B) and rates (FIG. 1C) of dsRed. The dark fraction ($f_1$=0.30+/−0.04) appears constant below saturation (with a minor decline at low $k_{ex}$ and the rate depends linearly on intensity with a slope of (2.9=/−0.2)×$10^{-3}$ and an intercept of 400=/−30 Hz as $k_{ex}$->0. Autocorrelation spectra of dsRed (FIG. 10A) at low $k_{ex}$ show lack of pH dependence in the pH range 3.9 to 11.

FIG. 10D shows the fluorescence flicker rate (1.7+/−0.1× $10^3$ $s^{-1}$) and dark fraction (0.41+/−0.03) are clearly independent of pH.

FIG. 11B) with the best fit (dotted line), and fractions (□; FIG. 11C) for proton binding. The pH-independent photoconversion rate $\tau_1^{-1}=1.6=/-0.4 \times 10^3 s^{-1}$ (○; FIG. 11B) and dark fraction (●; FIG. 11C) $f_1$=0.30+/−0.06 are superimposed.

DETAILED DESCRIPTION OF THE INVENTION

Figure 2B:
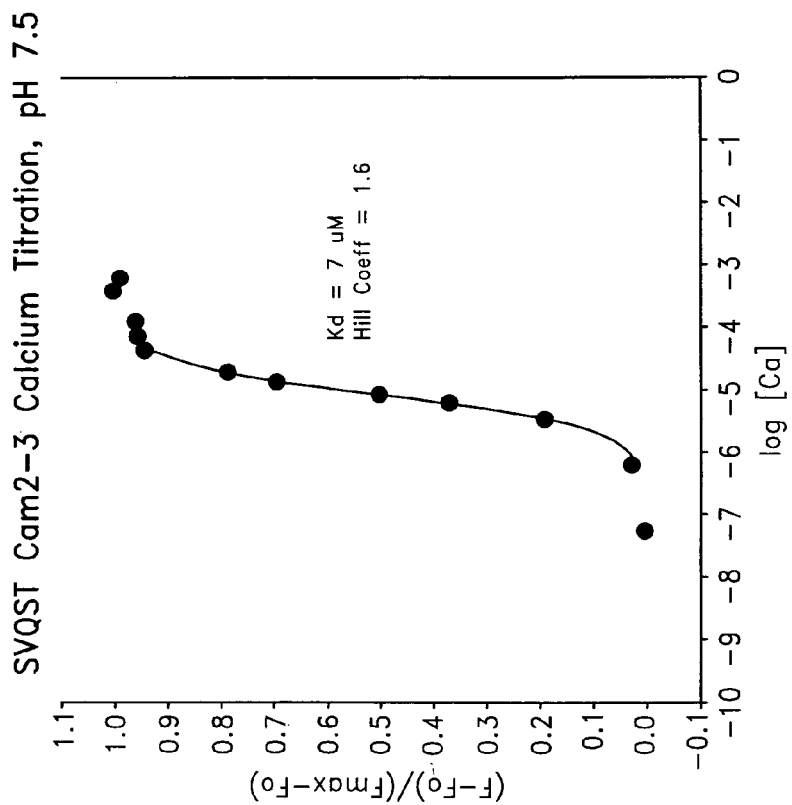
FIG. 2B shows titration curves for a calmodulin insertion indicator.

The present invention relates to polynucleotides encoding fluorescent indicators, fluorescent indicators having a sensor polypeptide, and methods of producing and using the same. As disclosed herein, a number of sites have been identified in *Aequorea*-related fluorescent protein moieties that are tolerant to insertions and rearrangements, and the insertion of sensory polypeptides into such sites results in polypeptides that are useful in detection of chemical, biological, electrical or physiological parameters, for example. Such insertion sites include, for example, one or more amino acids between residues 128–148, residues 155–160, residues 168–176 or residues 227–229 of the fluorescent protein moiety. Other positions that can tolerate insertions include, but are not limited to, residues 49–50, 78–79, 116–117, 134–135, 140–141, 157–158, 172–173, 194–195, 189–190 and 213–214 (see Abedi et al., *Nucleic Acids Research*, 26(2):623–630 (1998), which is incorporated herein by reference). More specifically, the insertion is a Y145. Using methods as disclosed herein, such insertion sites similarly can be identified in a *Discosoma* dsRed fluorescent protein.

As further disclosed herein, when a sensor polypeptide is inserted into an *Aequorea*-related fluorescent protein (e.g., GFP, YFP or CFP) or a mutant thereof (e.g., citrine) that provides a response related to an interaction with a biological, chemical, electrical or physiological parameter, the responsiveness results in a change in fluorescence of the fluorescent protein. As such, the present invention provides constructs that are useful in measuring interactions of a sensor polypeptides with environmental stimuli in vitro or in vivo, as well as methods of using such constructs. The constructs of the invention rely on, for example, detectable changes within a GFP-sensor-related protein itself to influence the actual fluorescence of the fluorophore and not the interaction of tandem fluorescent molecules. For example, when calmodulin is inserted into YFP at position Y145, interaction of calmodulin with its ligand (e.g., calcium) results in a change in the brightness of the fluorescent protein of between about 2-fold and 8-fold.

The indicators of the present invention are advantageous due to their reduced size as compared to FRET-based sensors. The reduced size has importance in allowing the indicator to measure chemical, biological, electrical or physiological interactions with the sensor polypeptide, for example, in subcellular compartments that are inaccessible to the larger, FRET-based sensors. In addition, the maximal change in fluorescence intensity observed in the present indicators (e.g., up to 8 fold increase) is much greater than the change in the cameleons (e.g., FRET-based sensors), which show about a 2 fold change in yellow to cyan intensity ratio.

Accordingly, the present invention provides polynucleotides and nucleic acid sequences encoding fluorescent indicators having a fluorescent protein moiety and a sensor polypeptide, or fragments thereof, inserted in operable association into the fluorescent protein moiety, in which the sensor polypeptide is responsive to an environmental parameter (e.g., a chemical, a biological, a electrical, or a physiological parameter). Accordingly, the responsiveness of the sensor polypeptide causes a change in fluorescence of the fluorescent indicator. The degree of change in the fluorescence of the indicator is sensitive to pH.

As used herein, the term "operatively inserted" or "operably inserted" refers to positioning at least one molecule between two amino acids of a polypeptide or between two nucleotides of a nucleic acid sequence such that one or more of the components are functional. Accordingly, the term excludes ligating or attaching a molecule such as a polypeptide to a naturally occurring amino or carboxy terminus amino acid of a polypeptide or 5' or 3' nucleotide in a nucleic acid sequence.

As used herein, the term "detectable change" or "responsiveness" means any response of a polypeptide to a chemical, biological, electrical, or physiological parameter or stimuli. A response can be a small change, for example, a shift in the orientation of an amino acid or peptide fragment of the sensor polypeptide as well as, for example, a change in the primary, secondary, or tertiary structure of a polypeptide, including for example, changes in protonation, electrical and chemical potential and or conformation. Thus, the term "responsive" encompasses, for example, any response of a polypeptide that is related to an interaction of a chemical, biological, electrical, or physiological parameter with a sensor polypeptide (e.g., conformational change in a voltage-gated ion channel (e.g., Shaker) in detection of membrane voltage across a biological membrane; phosphorylation of a hormone receptor resulting in a conformational change in the receptor upon hormone stimulation).

The term "conformation" refers to the three-dimensional arrangement of the primary, secondary and tertiary structure of a molecule, including side groups in the molecule; a change in conformation occurs when the three-dimensional structure of a molecule changes. Examples of conformational changes include a shift from $\alpha$-helix to a $\beta$-sheet or a shift from $\beta$-sheet to a $\alpha$-helix. It is understood that detectable changes need not be a conformational change, so long as the fluorescence of the fluorescent protein moiety is altered.

The term "fragments" as used herein refers to a portion of a naturally occurring sensor protein that can exist in at least two different states or conformations. Fragments can have the same or substantially the same amino acid sequence as the naturally occurring protein. The term "substantially the same" means that an amino acid sequence is largely, but not entirely, the same as a reference amino acid sequence, but retains a functional activity of the sequence to which it is related. In general two amino acid sequences are substantially the same or "substantially homologous" if they are at least 85% identical. Fragments which have different three dimensional structures as the naturally occurring protein are also included.

Where the fluorescent protein contains a second fluorescent protein and a sensor moiety within the insert, utilization of FRET based techniques to analyze or detect changes in chemical, biological or electrical parameters can be performed. For example, binding of an analyte such as calcium to a sensor polypeptide such as calmodulin changes the distance or angular orientation of the two fluorescent protein chromophores relative to each other, thereby modulating FRET. A circularly permuted fluorescent protein can be tandemly or insertionally fused via a sensor moiety to a second fluorescent protein, which itself optionally can be a circular permutation, such that the FRET between the two fluorescent proteins changes in response to chemical, biological, or electrical parameters.

Classes of sensor polypeptides that can be used in the compositions and methods of the invention include, but are not limited to, channel proteins, receptors, enzymes, and G-proteins. Example of sensor polypeptides useful in the present invention include calmodulin, a calmodulin-related protein moiety, recoverin, a nucleoside diphosphate or triphosphate binding protein, an inositol-1,4,5-triphosphate receptor, a cyclic nucleotide receptor, a nitric oxide receptor, a growth factor receptor, a hormone receptor, a ligand-binding domain of a hormone receptor, a steroid hormone receptor, a ligand binding domain of a steroid hormone receptor, a cytokine receptor, a growth factor receptor, a neurotransmitter receptor, a ligand-gated channel, a voltage-gated channel, a protein kinase C, a domain of protein kinase C, a cGMP-dependent protein kinase, an inositol polyphosphate receptor, a phosphate receptor, a carbohydrate receptor, an SH2 domain, an SH3 domain, a PTB domain, an antibody, an antigen-binding site from an antibody, a single-chain antibody, a zinc-finger domain, a protein kinase substrate, a protease substrate, a phosphorylation domain, a redox sensitive loop, a loop containing at least two cysteines that can form a cyclic disulfide, and a fluorescent protein moiety.

Channel polypeptides useful for purposes of the invention include, but are not limited to, voltage-gated ion channels including the potassium, sodium, chloride, G-protein-responsive, and calcium channels. A "channel polypeptide" is typically a polypeptide embedded in a cell membrane, and is or is part of a structure that determines what particle sizes and/or charges can traverse the cell membrane. Channel polypeptides include the "voltage-gated ion channels", which are proteins imbedded in a cell membrane that serve as a crossing point for the regulated transfer of a specific ion or group of ions across the membrane. Specifically, Shaker potassium channels or dihydropuridine receptors from skeletal muscle can be advantageously used in the present invention. Several ion channel polypeptides of use with the invention are listed in Table 1.

TABLE 1

Ion Channels

| Gene Product | GenBank Accession No. |
|---|---|
| Human voltage-gated chloride ion channel CLCN5 | X91906 |
| Human delayed rectifier potassium channel (Isk) gene | L33815 |
| Human potassium channel protein (HPCN3) gene | M55515 |
| Human potassium channel (HPCN2) (mRNA) | M55514 |
| Human potassium channel (HPCN1) (mRNA) | M55513 |
| Human gamma subunit of epithelial amiloride-sensitive sodium channel (mRNA) | X87160 |
| Human beta subunit of epithelial amiloride-sensitive sodium channel | X87159 |

Channels also include those activated by intracellular signals such as those where the signal is by binding of ligand such as calcium, cyclic nucleotides, G-proteins, phosphoinositols, arachidonic acid, for example, and those where the signal is by a covalent modification such as phosphorylation, enzymatic cleavage, oxidation/reduction, and acetylation, for example. Channel proteins also include those activated by extracellular ligands (e.g., ionotropic receptors). These can be activated by acetylcholine, biogenic amines, amino acids, and ATP, for example.

A "receptor polypeptide" is a polypeptide found within or on a cell, often on a membrane, that can combine with a specific type of molecule, e.g., a ligand, and alter a function of the cell. Receptor polypeptides of use with the invention include, but are not limited to, the growth factor receptors, hormone receptors, cytokine receptors, chemokine receptors, neurotransmitter receptors, ligand-gated channels, and steroid receptors. Specifically, polypeptides encoding insulin-like growth factor, insulin, somatostatin, glucagon, interleukins, e.g., IL-2, transforming growth factors (TGF-$\alpha$, TGF-$\beta$), platelet-derived growth factor (PDGF), epidermal growth factor (EGF), nerve growth factor (NGF), fibroblast growth factor (FGF), interferon-$\gamma$ (IFN-$\gamma$), and GM-CSF receptors are of use with the invention. Receptors such as those where binding of ligand is transmitted to a G-protein (e.g., for 7-transmembrane receptors) or kinase domains (for single transmembrane receptors) can be used with the invention. These can be activated by acetylcholine, biogenic amines, amino acids, ATP, and many peptides, such as opioids, hypothalamic-releasing hormones, neurohypophyseal hormones, pituitary hormones, tachykinins, secreting, insulins, somatostatins, and gastrointestinal peptides. Several receptor polypeptides of use with the invention are listed in Table 2.

TABLE 2

Receptors

| Gene Product | GenBank Accession No. |
|---|---|
| Human insulin receptor gene | M29929 |
| Human somatostatin receptor gene | L14856 |
| Human IL-2 receptor gene | X01057, X01058, XD1402 |
| Human TGF receptor (mRNA) | M8509 |
| Human PDGF receptor (mRNA) | M22734 |
| Human EGF receptor gene | X06370 |
| Human NGF receptor (mRNA) | M14764 |
| Human FGF receptor (mRNA) | M34641 |
| Human GM-CSF receptor (mRNA) | M73832 |
| Human IFN-$\gamma$ receptor (mRNA) | X62468 |

An "enzyme" is a polypeptide that acts as a catalyst that accelerates the rate at which biochemical reactions proceed, generally without altering the direction or nature of the reaction. Enzyme polypeptides useful in the invention include, but are not limited to, protein kinases, catalyses, amidase, phosphatases, guanylyl and adenylyl cyclases, and lipoxygenases. Polypeptides encoding the serine/threonine protein kinases are of use with the invention. Several genes encoding human enzymes of use with the invention are listed in Table 3.

TABLE 3

Enzymes

| Gene Product | GenBank Accession No. |
|---|---|
| Human cAMP dependent protein kinase AKAD 79 (mRNA) | M90359 |
| Human protein kinase C beta gene | D10022 |
| Human lipid-activate protein kinase PRK-1 (mRNA) | U33053 |
| Human guanine nucleotide binding protein alpha subunit gene | M21142, J03647, M21139 |
| Human serine/threonine kinase (mRNA) | M83780 |

As disclosed herein, the responsiveness of a sensor polypeptide (e.g. a change in conformation or state) that occurs in response to interaction of the sensor polypeptide with a chemical, biological, electrical or physiological parameter can cause a change in fluorescence of the fluorescence indicator. The change can be the result of an alteration in the environment, structure, protonation or oligomerization status of the fluorescent indicator or chromophore. The molecular component responsible for a conformational change is known for many enzymes (e.g., Blostien et al. (1997) *J. Biol. Chem.*, 272:24987–93; Shoelstein et al., (1993) *EMBO J.*, 12:795–802), receptors (e.g. Moyle et al., (1995) *J. Biol. Chem.*, 270:20020–20031; Baron et al., (1992), *J. Biol. Chem.* 267:23290–23294), and channels (e.g., Bouzat et al., (1994) *Neuron*, 13:1395–1402; Dulhanty, (1994) *Biochemistry*, 33:4072–79) polypeptide. The optical properties (e.g., fluorescence) of the indicator that can be altered in response to the conformational change in the sensor polypeptide include, but are not limited to, changes in the excitation or emission spectrum, quantum yield, extinction coefficient, excited life-time and degree of self-quenching for example. The cause of the changes in these parameters can include, but are not limited to, changes in the environment, changes in the rotational or vibrational freedom of the sensor, changes in the angle of the sensor with respect to the exciting light or the optical detector apparatus, changes in the protonation or deprotonation of amino acids or side groups associated with a chromophore or changes in distance or dipole orientation between sensors on associated responsive polypeptides.

For example, insertion of a peptide or protein in place of tyrosine-145 (Y145) in mutants of GFP increases the sensitivity of fluorescence to quenching by acidic pH. When the inserted sensor polypeptide responds to a chemical, biological, electrical, or physiological parameter and undergoes a detectable change (e.g., a change in conformation), such interactions change the fluorescence via a shift in the acid sensitivity. For example, when calmodulin, a calcium sensing protein, replaces residue Y145 in a yellow mutant of GFP, calcium binding increases the fluorescence by up to 8-fold, depending on the pH at which the measurement is made. Other sites for insertion into GFP or GFP-mutants are allowable where circular permutation is tolerated, as discussed more fully below.

In the fluorescent indicator proteins of the invention, the sensor polypeptide is operably inserted into an optically active polypeptide (e.g., a fluorescent protein moiety). A protein-based "optically active polypeptide" is a polypeptide that can emit light. Fluorescence is one optical property of an optically active polypeptide that can provide a means of detecting the responsiveness of the sensor or responsive polypeptide of the fluorescent indicator or circularly permuted fluorescent proteins of the invention. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between the active and inactive states suffices for the utility of the fluorescent protein substrates of the invention in assays for activity. A measurable difference can be determined by determining the amount of any quantitative fluorescent property, e.g., the amount of fluorescence at a particular wavelength, or the integral of fluorescence over the emission spectrum. Optimally, the protein substrates are selected to have fluorescent properties that are easily distinguishable in the un-activated and activated conformational states.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. For example, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. Other means of measuring fluorescence can also be used with the invention.

Methods of performing assays on fluorescent materials are well known in the art and are described in, e.g., Lakowicz, *Principles of Fluorescence Spectroscopy*, Plenum Press (1983); Herman, Resonance energy transfer microscopy, in: *Fluorescence Microscopy of Living Cells in Culture, Part B, Methods in Cell Biology*, vol. 30, ed. Taylor & Wang, San Diego: Academic Press (1989), pp. 219–243; Turro, *Modern Molecular Photochemistry*, Menlo Park: Benjamin/Cummings Publishing Col, Inc. (1978), pp. 296–361.

Any fluorescent protein can be used for purposes of the present invention, including, for example, proteins that fluoresce due to intramolecular rearrangements or to the addition of cofactors that promote fluorescence. For example, green fluorescent proteins of cnidarians, which act as energy-transfer acceptors in bioluminescence, are suitable fluorescent proteins for use in the fluorescent indicators. A green fluorescent protein ("GFP") is a protein that emits green light, a blue fluorescent protein ("BFP") is a protein that emits blue light, a yellow fluorescent protein ("YFP") is one that emits yellow light, a cyan fluorescent protein ("CFP") is one that emits a greenish-blue light, and a red fluorescent protein is one that emits red light. GFPs have been isolated from the Pacific Northwest jellyfish, *Aequorea victoria*, the sea pansy, *Renilla reniformis*, and *Phialidium gregarium*. See, Ward et al, *Photochem. Photobiol.*, 35:803–808 (1982); and Levine et al., *Comp. Biochem. Physiol.*, 72B:77–85 (1982). The red fluorescent protein, dsRed, has been isolated from coral of the genus *Discosoma* (see, for example, Baird et al., *Proc. Natl. Acad. Sci., USA* 97:11984–11989 (2000); Gross et al., *Proc. Natl. Acad. Sci., USA* 97:11990–11995 (2000), each of which is incorporated herein by reference).

A variety of *Aequorea*-related GFPs having useful excitation and emission spectra have been engineered by modifying the amino acid sequence of a naturally occurring GFP from *Aequorea victoria*. (See, Prasher et al., *Gene*, 111: 229–233 (1992); Heim et al., *Proc. Natl. Acad. Sci., USA*, 91:12501–04 (1994); U.S. Pat. Nos. 5,491,084 and 5,625, 048; International application PCT/US95/14692, filed Nov. 10, 1995). The cDNA of a GFP can be concatenated with cDNA molecule(s) encoding one or more other proteins; the resulting chimerics often are fluorescent and retain the biochemical features of the partner proteins. (See, Cubitt et al, *Trends Biochem. Sci.* 20:448–455 (1995)). Mutagenesis studies have produced may GFP mutants, some having shifted wavelengths of excitation or emission (see, Heim & Tsien,. *Current Biol.* 6:178–182 (1996)). Suitable pairs, for example a blue-shifted GFP mutant P4-3 (Y66H/Y145F) and an improved green mutant S65T can respectively serve as a donor and an acceptor for fluorescence resonance energy transfer (FRET). (See, Tsien et al., *Trends Cell Biol.* 3:242–245 (1993)). Any of such proteins can be included in a sensor of the invention.

A fluorescent protein is an "*Aequorea*-related fluorescent protein" if any contiguous sequence of 150 amino acids of the fluorescent protein has at least 85% sequence identity with an amino acid sequence, either contiguous or non-contiguous, from the wild type *Aequorea* green fluorescent protein. Preferably, an *Aequorea*-related fluorescent protein contains a contiguous sequence of at least about 200 amino acids of the fluorescent protein having at least 95% sequence identity with an amino acid sequence, either contiguous or non-contiguous, from the corresponding wild type *Aequorea* green fluorescent protein. For example, with respect to circularly permuted fluorescent proteins, any continuous sequence of the circularly permuted sequence that has identity to an *Aequorea*-related fluorescent protein, as described above, whether further N-terminal or C-terminal than the comparison sequence, is considered related. Similarly, the fluorescent protein can be related to *Renilla* or *Phialidium* wild-type fluorescent proteins using the same standards. Some *Aequorea*-related engineered versions described in Table 4. Other variants or mutants are within the scope of the invention as described, for example, in the Examples.

An additional clone, W1B1 included the following mutations: F64L; S65T; Y66W; F99S; and V163A.

Other fluorescent proteins can be used in the fluorescent indicators, including, for example, yellow fluorescent protein from *Vibrio fischeri* strain Y-1, Peridinin-chlorophyll α binding protein from the dinoflagellate *Symbiodinium* sp. phycobiliproteins from marine cyanobacteria such as *Synechococcus*, e.g., phycoerythrin and phycocyanin, or oat phytochromes from oat reconstructed with phycoerythrobilin. These fluorescent proteins have been described in Baldwin et al., *Biochemistry* 29:5509–5515 (1990), Morris et al., *Plant Molecular Biology*, 24:673–677 (1994), and Wilbanks et al., *J. Biol. Chem.* 268:1226–1235 (1993), and Li et al., *Biochemistry* 34:7923–7930 (1995), Murphy & Lagarias, *Current Biology* 7:870–876 (1997).

The fluorescent indicators can be produced as chimeric proteins by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from *A. victoria* using primers based on the DNA sequence of *A. victoria* green fluorescent protein. PCR methods are described in, for example, U.S. Pat. No. 4,683,195; Mullis, et al. *Cold Spring Harbor Symp. Quant. Biol.* 51:263 (1987), and Erlich, ed., *PCR Technology*, (Stockton Press, NY, 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In the chimeric proteins of the invention, the sensor polypeptide is operably inserted to an optically active polypeptide, which responds (e.g., a conformation change), for example, to a cell signaling event. Cell signaling events that occur in vivo can be of very short duration. The optically active polypeptides of the invention allow measurement of the optical parameter, such as fluorescence, which is altered in response to the cell signal, over the same time period that the event actually occurs. Alternatively, the response can be measured after the event occurs (over a

TABLE 4

| Clone | Mutation(s) | Excitation max (nm) | Emission max (nm) | Extinction Coefficient ($M^1 cm^{-1}$) | Quantum yield |
|---|---|---|---|---|---|
| Wild type | none | 395 (475) | 508 | 21,000 (7,150) | 0.77 |
| P4 | Y66H | 383 | 447 | 13,500 | 0.21 |
| P4-3 | Y66H; Y145F | 381 | 445 | 14,000 | 0.38 |
| W7 | Y66W; N1461 M153T V163A N212K | 433 (453) | 475 (501) | 18,000 (17,100) | 0.67 |
| W2 | Y66W; I123V Y145H H148R M153T V163A N212K | 432 (453) | 480 | 10,000 (9,600) | 0.72 |
| S65T | S65T | 489 | 511 | 39,200 | 0.68 |
| P4-1 | S65T; M153A K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G; V68L S72A; T203Y | 513 | 527 | | |
| W1B | F64L; S65T Y66W; N1461 M153T V163A N212K | 432 (453) | 476 (503) | | |
| Emerald | S65T; S72A N149K M153T I167T | 487 | 508 | | |
| Sapphire | S72A; Y145F T203I | 395 | 511 | | | longer time period) as the response that occurs in an optically active polypeptide can be of a longer duration than the cell signaling event itself.

Nucleic Acid Constructs of the Invention

In another embodiment, the invention provides isolated nucleic acid sequences that encode fluorescent indicator polypeptides having operatively inserted therein a sensor polypeptide, or fragment thereof, which normally exists in one state e.g., conformational shape or charge, prior to an interaction with a chemical, biological, electrical or physiological parameter at which time it undergoes a response during or after the interaction of the chemical, biological, electrical or physiological parameter with the sensor polypeptide.

The term "polynucleotide" or "nucleic acid sequence" refers to a polymeric form of nucleotides at least 10 bases in length. By "isolated nucleic acid sequence" is meant a polynucleotide that is no longer immediately contiguous with both of the coding sequences with which it was immediately contiguous (one on the 5' end and one on the 3' end) in the naturally occurring genome of the organism from which it is derived. As such, the term "isolated nucleic acid sequence" includes, for example, a recombinant DNA, which can be incorporated into a vector, including an autonomously replicating plasmid or virus; or into the genomic DNA of a prokaryotic or eukaryotic cell or organism; or that exists as a separate molecule (e.g. a CDNA) independent of other sequences. The nucleotides of the invention can be ribonucleotides, deoxyribonucleotides, or modified forms thereof, and the polynucleotides can be single stranded or double stranded.

A nucleic acid sequence that encodes a fluorescent indicator of the invention, wherein the indicator includes a sensor polypeptide, or fragment thereof, which normally has two or more states or conformational arrangements, and which undergoes a response during interaction with a chemical, biological, electrical or physiological parameter, can be operatively linked to expression control sequences. The term "operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding nucleic acid sequence, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and chimeric partner sequences. Expression control sequences can include a promoter.

The term "promoter" refers to a minimal sequence sufficient to direct transcription. Also included in the invention are those promoter elements that are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter; CMV promoter) may be used. Promoters produced by recombinant DNA or synthetic techniques may also be used to provide for transcription of the nucleic acid sequences of the invention.

The term "fluorescent protein" and "fluorescent protein moiety" are used interchangeably and refer to any protein capable of emitting light when excited with appropriate electromagnetic radiation, and which has an amino acid sequence that is either natural or engineered and is derived from the amino acid sequence of an *Aequorea*-related fluorescent protein. The term "fluorescent indicator" refers to a fluorescent protein including a sensor polypeptide, and whose emitted light varies with the response state or conformation of the sensor polypeptide upon interaction with a chemical, biological, electrical or physiological parameter. The term also refers to a fluorescent protein whose amino acid sequence has been circularly permuted. The fluorescent indicators of the invention are also sensitive to pH in the range of about 5 to about 10. Thus, the invention provides, for example, a functional engineered fluorescent protein indicator whose amino acid sequence is substantially identical to the 238 amino acid *Aequorea victoria* green fluorescence protein (SEQ ID NO:3).

The invention also includes functional polypeptide fragments of a fluorescent indicator. As used herein, the term "functional polypeptide fragment" refers to a polypeptide which possesses biological function or activity which is identified through a defined functional assay. The term "functional fragments of a functional engineered fluorescent protein" refers to fragments of a functional engineered protein that retain a function of the engineered fluorescent protein, e.g., the ability to fluoresce in manner which is dependent upon interactions of a chemical, biological, electrical or physiological parameter with a sensor polypeptide over the pH range 5 to 10.

Minor modifications of the functional engineered fluorescent indicator can result in proteins that have substantially equivalent activity as compared to the unmodified counterpart polypeptide as described herein. Such modifications may be deliberate, as by site-directed mutagenesis, or may be spontaneous. All of the polypeptides produced by these modifications are included herein as long as fluorescence of the engineered protein still exists.

By "substantially identical" or "substantially homologous" is meant a protein or polypeptide that retains the activity of a functional engineered fluorescent indicator, or nucleic acid sequence or polynucleotide encoding the same, and which exhibits at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. The reference amino acid sequence or nucleic acid sequence is considered homologous if the reference amino acid sequence is 80–95% homologous to any portion of the amino acid or nucleic acid sequence in question. For example, where a circularly permuted polypeptide sequence has been generated, the sequence will typically have an amino acid sequence wherein a carboxy terminal sequence is now more amino terminal than the original fluorescent protein. In such instances, the circularly permuted sequence is considered homologous because the carboxy terminal sequence is still present in the circularly permuted fluorescent protein even though it is now more N-terminal.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (e.g., assayed as described herein). Preferably, such a sequence is at least 85%, more preferably 90%, more preferably 95%, more preferably 98%, and most preferably 99% identical at the amino acid sequence to one of the sequences of EGFP (SEQ ID NO:4), EYFP (SEQ ID NO:5), ECFP (SEQ ID NO:7), EYFP-V68L/Q69K (SEQ ID NO:6), YFP H148G (SEQ ID NO:8), YFP H148Q (SEQ ID NO:9), or citrine (SEQ ID NO:65). Circularly permuted sequences fall within the definition of "substantially identical" if, for example, one or more amino acids of a circularly permuted polypeptide sequence is changed as described herein.

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

In some embodiments, the amino acid sequence of the protein includes one of the following sets of substitutions in the amino acid sequence of the *Aequorea* green fluorescent protein (SEQ ID NO:3): F64L/S65T/H231L, referred to herein as EGFP (SEQ ID NO:4); S65G/S72A/T203Y/H231L, referred to herein as EYFP (SEQ ID NO:5); S65G/V68L/Q69K/S72A/T203Y/H231L, referred to herein as EYFP-V68L/Q69K (SEQ ID NO:6); and K26R/F64L/S65T/Y66W/N146I/M153T/V163A/N164H/H231L, referred to herein as ECFP (SEQ ID NO:7). The numbering of the amino acids conforms to that in native *Aequorea* GFP. Thus, the first serine is amino acid number 2 even if a valine (amino acid no. 1a) has been inserted to optimize ribosome initiation. Thus, F64L corresponds to a substitution of leucine for phenylalanine in the 64th amino acid following the initiating methionine.

In other embodiments, the amino acid sequence of the protein is based on the sequence of the wild-type *Aequorea* green fluorescent protein, but includes the substitution H148G (GFP-H148G) or H148Q (GFP-H148Q). In specific embodiments, these substitutions can be present along with other substitutions, e.g., the proteins can include the substitutions S65G/V68L/S72A/H148G/Q80R/T203Y (SEQ ID NO:8), which is referred to herein as the "YFP H148G mutant," S65G/V68L/S72A/H148Q/Q80R/T203Y, which is referred to herein as the "YFP H148Q mutant" (SEQ ID NO:9), the as well as EYFP-H148G (SEQ ID NO: 10) and EYFP-H148Q (SEQ ID NO:11).

In still other embodiments, the fluorescent protein is the *Aequorea*-related fluorescent protein, citrine (SEQ ID NO:65), or is based on the sequence of the wild-type *Discosoma* red fluorescent protein, dsRed, which has the amino acid sequence set forth in SEQ ID NO:67. As disclosed herein, the photophysics of dsRed and the improved yellow fluorescent protein mutant (citrine) (S65G/V68L/Q69M/S72A/T203Y) were characterized and compared using fluorescence correlation spectroscopy (FCS) and time-correlated single-photon counting (see Example 2). dsRed fluorescence decayed as a single exponential with a 3.65+/−0.07 nanosecond (ns) time constant, indicating a single emitting state/species independent of pH 4.4–9.0, in contrast with citrine. However, laser excitation drove reversible fluorescence flicker at $10^3$–$10^4$ Hz between dark and bright states with a constant partition fraction $f_1$=0.42+/−0.06 and quantum yield of $\approx 3 \times 10^{-3}$. Unlike citrine (pKa≈5.7), pH-dependent proton binding is negligible (pH 3.911) in dsRed. Time-resolved anisotropy of dsRed revealed rapid depolarization (211+/−6 ps) plus slow rotational motion (53+/−8 ns), in contrast with a single rotational time (16+/−2 ns) for citrine. The molecular dimensions, calculated from rotational and translational diffusion, indicated that dsRed is hydrodynamically 3.8+/−0.4 times larger than predicted for a monomer, indicating an oligomer (possibly a tetramer) configuration even at $\approx 10^{-9}$ M. The fast depolarization was attributed to intraoligomer energy transfer between mobile nonparallel chromophores with the initial anisotropy implying a 24+/−3° depolarization angle. Large two-photon excitation cross sections (≈100 GM at 990 nm for dsRed and ≈50 GM at 970 mn for citrine) were measured, and are advantageous for two-photon-fluorescence imaging in cells.

dsRed (SEQ ID NO:67) provides intrinsic red-shifted absorption and emission that are desirable features in a noninvasive fluorescent label for multiphoton and conventional fluorescence microscopy imaging for biological studies of intracellular activities. Furthermore, dsRed can be used as an acceptor in a fluorescence resonance energy transfer (FRET) pair with enhanced green fluorescent protein (EGFP) or yellow fluorescent protein (YFP) mutants. Citrine (S65G/V68L/Q69M/S72A/T203Y; SEQ ID NO:65), which has one of the longest wavelength mutants of the GFPs, was compared with dsRED (Example 2). Citrine is identical in sequence to the reported mutant 10C (Tsien, *Ann. Rev. Biochem.* 67:509–544 (1998), which is incorporated herein by reference) except for replacement of Gln-69 by Met, which confers several useful properties. Compared with other yellow GFP mutants, citrine is more resistant to acid quenching, less sensitive to chloride, and more easily expressible at 37° C.

Fluorescence correlation spectroscopy (FCS) (Magde et al., *Phys. Rev. Lett.* 29:705–708 (1972); Maiti et al., *Proc. Natl. Acad. Sci., USA* 94:11753–11757 (1997), Eigen and Rigler, *Proc. Natl. Acad. Sci., USA* 91:5470–5477 (1994)) provides an elegant method to probe the diffusion times ($\tau_D$) of fluorophores in an optically defined excitation volume (beam waist $1/e^2 \approx R$) and thus the molecular diffusion coefficient (D) can be calculated by using $\tau_D \propto R^2/4D$. Furthermore, inter- and intramolecular dynamics that influence the fluorescence characteristics on a time scale faster than $\tau_D$ can be measured (Elson and Magde, *Biopolymers* 13:1–27 (1974)). Fluorescence flicker of EGFP because of reversible binding of an external proton to the chromophore occurs on a tens-of-microseconds time scale (Haupts et al., *Proc. Natl. Acad. Sci., USA* 95:13573–13578 (1998)), and the rate constants, pKa, enthalpy, and entropy of the reaction were characterized. An additional flicker, with a mean dark fraction ≈13%, slightly sensitive to the illumination intensity, was also observed independent of pH. These findings triggered studies discovering fast intensity-dependent and pH-dependent flicker in T203Y and T203F by using FCS (Schwille et al., *Proc. Natl. Acad. Sci., USA* 97:151–156 (2000), which is incorporated herein by reference). The goal was to separate the two effects (pH and intensity) on the protein fluorescence flicker and to compare with the slow (a few seconds) fluorescence blinking, reported by Dickson et al. (*Nature* 388:355–358 (1997)) on immobilized individual proteins. The on/off switching was attributed to photoconversion among the anionic, intermediate, and neutral states of the chromophore (Dickson et al., supra, 1997).

dsRed and citrine were examined using FCS to measure D, photobleaching quantum yield ($\Phi_B$), proton-binding kinetics, and light-driven flicker, as the protein undergoes photoconversion between bright and dark states (Example 2). The excited state dynamics are also studied by using time-correlated single-photon counting (TCSPC; O'Connor and Phillips, in Time-Correlated Single Photon Counting (Academic Press 1984), which is incorporated herein by reference). As an adequate representation of the results, the "dark" state, to be called the "neutral" state, was associated with both the externally protonated neutral molecule and the essentially neutral states of the chromophore (i.e., the chromophore plus the surrounding hydrogen-bond network in the protein environment) within the anionic protein. The "bright" state was associated with the unprotonated molecular anion to be called the "anionic" state. Because multiphoton fluorescence microscopy (Denk et al., in Handbook of Biological Confocal Microscopy, ed. Pawley (Plenum 1995)) is particularly suited for intracellular studies, the two-photon (2P) excitation cross-section spectra of both dsRed and citrine were also measured.

In some embodiments, the protein or polypeptide is substantially purified. By "substantially pure protein or polypeptide" is meant an functional engineered fluorescent polypeptide which has been separated from components which naturally accompany it. Typically, the protein or polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of the protein. A substantially pure protein may be obtained, for example, by extraction from a natural source (e.g., a plant cell); by expression of a recombinant nucleic acid encoding a functional engineered fluorescent protein; or by chemically synthesizing the protein. Purity can be measured by any appropriate method, e.g., those described in column chromatography, polyacrylamide gel electrophoresis, or by HPLC analysis.

A protein or polypeptide is substantially free of naturally associated components when it is separated from those contaminants which accompany it in its natural state. Thus, a protein or polypeptide which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

The invention also provides polynucleotides encoding the functional engineered fluorescent protein described herein. These polynucleotides include DNA, cDNA, and RNA sequences which encode functional engineered fluorescent proteins. It is understood that all polynucleotides encoding functional engineered fluorescent proteins are also included herein, as long as they encode a protein or polypeptide whose fluorescent emission intensity changes as pH varies between 5 and 10. Such polynucleotides include naturally occurring, synthetic, and intentionally manipulated polynucleotides. For example, the polynucleotide may be subjected to site-directed mutagenesis. The polynucleotides of the invention include sequences that are degenerate as a result of the genetic code. Therefore, all degenerate nucleotide sequences are included in the invention as long as the amino acid sequence of the functional engineered fluorescent protein or derivative is functionally unchanged.

Specifically disclosed herein is a polynucleotide sequence encoding a functional engineered fluorescent protein that includes one of the following sets of substitutions in the amino acid sequence of the *Aequorea* green fluorescent protein (SEQ ID NO:3): S65G/S72A/T203Y/H231L, S65G/V68L/Q69K/S72A/T203Y/H231L; K26R/F64L/S65T/Y66W/N146I/M153T/V163A/N164H/H231L; S65G/V68L/Q69M/S72A/T203Y. In specific embodiments, the DNA sequences encoding EGFP, EYFP, ECFP, EYFP-V68L/Q69K, YFP-H148G, YFP-H148Q, and citrine are shown as SEQ ID NOS:12 to 19 and 64, respectively.

The nucleic acid encoding functional engineered fluorescent proteins may be chosen to reflect the codon choice in the native *A. victoria* coding sequence, or, alternatively, may be chosen to reflect the optimal codon frequencies used in the organism in which the proteins will be expressed. Thus, nucleic acids encoding a target functional engineered protein to be expressed in a human cell may have use a codon choice that is optimized for mammals, or especially humans.

The functional engineered fluorescent protein can also include a targeting sequence to direct the fluorescent protein to particular cellular sites by fusion to appropriate organellar targeting signals or localized host proteins. A polynucleotide encoding a targeting sequence can be ligated to the 5' terminus of a polynucleotide encoding the fluorescence such that the targeting peptide is located at the amino terminal end of the resulting fusion polynucleotide/polypeptide. The targeting sequence can be, e.g., a signal peptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties are known to those skilled in the art, or can be readily ascertained using well known and routine methods.

In the present invention, the nucleic acid sequences encoding the fluorescent indicator or circularly permuted fluorescent protein of the invention may be inserted into a recombinant expression vector. The term "recombinant expression vector" refers to a plasmid, virus or other vehicle known in the art that has been manipulated by insertion or incorporation of the nucleic acid sequences encoding the chimeric peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene*, 56:125, 1987), the pMSXND expression vector, or adeno or vaccinia viral vectors for expression in mammalian cells (Lee and Nathans, *J. Biol. Chem.*, 263:3521, 1988), baculovirus-derived vectors for expression in insect cells, cauliflower mosaic virus, CaMV; tobacco mosaic virus, TMV.

The nucleic acid sequences encoding a fluorescent indicator or circularly permuted fluorescent protein of the invention can also include a localization sequence to direct the indicator to particular cellular sites by fusion to appropriate organellar targeting signals or localized host proteins. A polynucleotide encoding a localization sequence, or signal sequence, can be ligated or fused at the 5' terminus of a polynucleotide encoding the fluorescence indicator such that the signal peptide is located at the amino terminal end of the resulting chimeric polynucleotide/polypeptide. In the case of eukaryotes, the signal peptide is believed to function to transport the chimeric polypeptide across the endoplasmic reticulum. The secretory protein is then transported through the Golgi apparatus, into secretory vesicles and into the extracellular space or, preferably, the external environment. Signal peptides that can be utilized according to the invention include pre-propeptides which contain a proteolytic enzyme recognition site. Other signal peptides with similar properties to those described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", Chapter 35 of Stryer, *Biochemistry* (4th ed.), W. H. Freeman, 1995. The localization sequence can also be a localized protein. Some important localization sequences include those targeting the nucleus (KKKRK; SEQ ID NO:20), mitochondrion (amino terminal MLRTSSLFTRRVQPSLFRNILRLQST-; SEQ ID NO:21), endoplasmic reticulum (KDEL; SEQ ID NO:22) at C-terminus, assuming a signal sequence present at N-terminus), peroxisome (SKF at C-terminus), synapses (S/TDV or fusion to GAP 43, kinesin and tau) prenylation or insertion into plasma membrane (CAAX (SEQ ID NO:23), CC, CXC, or CCXX (SEQ ID NO:24) at C-terminus), cytoplasmic side of plasma membrane (chimeric to SNAP-25), or the Golgi apparatus (chimeric to furin). The construction of expression vectors and the expression of genes in transfected cells involves the use of molecular cloning techniques also well known in the art (see, for example, Sambrook et al., *Molecular Cloning: A Laboratory Manual* (Cold Spring Harbor Laboratory Press 1989); and *Current Protocols in Molecular Biology*, Ausubel et al., eds. (Greene Publishing Associates, Inc., and John Wiley & Sons, Inc., 1994, and most recent Supplement). These methods include in vitro recombinant DNA techniques, synthetic techniques and in vivo recombination/genetic recombination. (See, for example, Sambrook et al., supra, 1989).

Examples of agents which induce a sensor polypeptide, include agents that contain any of the amino acid sequences in Table 5, or a portion thereof with the proviso that the parameter must bind to a calmodulin sensor polypeptide. The parameter can be a subsequence of a calmodulin-binding domain. The moieties listed in Table 5 are recognized by the sensor polypeptide CaM. See, for example, Crivici & Ikura, *Ann. Rev. Biophys. Biomol. Struct.* 24:84–116 (1995). The parameter can be modified to enhance the response of the fluorescent indicator to the parameter. Other parameter are known in the art for other sensor polypeptides.

TABLE 5

| Target[a] | Sequence |
| --- | --- |
| skMLCK (M13) | KRRWKKNFIAVSAANRFKKISSSGAL (25*) |
| smMLCK (smMLCKp) | ARRKWQKTGHAVRAIGRLSS (26) |
| CaMKII | ARRKLKGAILTTMLATRNFS (27) |
| Caldesmon | GVRLNIKSMWEKGNVFSS (28) |
| Calspermin | ARRKLKAAVKAVVASSRLGS (29) |
| PFK (M11) | FMNNWEVYKLLAHIRPPAPKSGSYTV (30) |
| Calcineurin | ARKEVIRNKIRAIGKMARVFSVLR (31) |
| PhK (PhK5) | LRRLIDAYAFRIYGHWVKKGQQQNRG (32) |
| (PhK13) | RGKFKVICLTVLASVRIYYQYRRVKPG (33) |
| $Ca^{2+}$-ATPase (C28W) | LRRGQILWFRGLNRIQTQIKVVNAFSSS (34) |
| 59-kDa PDE | RRKHLQRPIFRLRCLVKQLEK (35) |
| 60-kDa PDE | TEKMWQRLKGILRCLVKQLEK (36) |
| NOS (NO-30) | KRRAIGFKKLAEAVKFSAKLMGQ (37) |
| Type I AC (AC-28) | IKPAKRMKFKTVCYLLVQLMHCRKMFKA (38) |
| *Borderella periussis* AC | IDLLWKIARAGARSAVGTEA (39) |

TABLE 5-continued

| Target[a] | Sequence |
|---|---|
| Neuromodulin | KAHKAATKIQASFRGHITRKKLKGEKK (40) |
| Spectrin | KTASPWKSARLMVHTVATFNSIKE (41) |
| MARCKS | KKKKKRFSFKKSFKLSGFSFKKSKK (42) |
| F52 or MacMARKS | KKKKKFSFKKPFKLSGLSFKRNRK (43) |
| β-Adducin | KQQKEKTRWLNTPNTYLRVNVADEVQRNMGS (44) |
| HSP90a | KDQVANSAFQERLRKHGLEVI (45) |
| HIV-1 gp160 | YHRLRDLLLIVKRIVELLGRR (46) |
| BBMHBI | QQLATLIQKTYRGWRCRTHYQLM (47) |
| Dilute MHC | RAACIRIQKTIRGWLLRKRYLCMQ (48) |
| Mastoparan | INLKALAALAKKIL (49) |
| Melittin | GIGAVLKVLTTGLPALISWIKRKRQQ (50) |
| Glucagon | HSQGTFTTSDYSKYLDSRRAQDFVQWLMNT (51) |
| Secretin | HSDGTFTSELSRLRDSARLQRLLQGLV (52) |
| VIP | HSDAVFTDNYTRLRKQMAVKKYLNSILN (53) |
| GIP | YADGTFISDYSAIMNKIRQQDFVNWLLAQQQKS (54) |
| Model Peptide CBP2 | KLWKKLLKLLKKLLKLG (55) |

*Number in parentheses is SEQ ID NO:.
[a]Abbreviations: AC, adenylyl cyclase; BBM-HCI, brush-border myosin heavy chain-I; CaMKII, calmodulin kinase II; CBP2, calmodulin binding peptide-2; GIP, gastrin inhibitory peptide; HIV-1 gp160, human immunodeficiency virus envelope glycoprotein 160; HSP, heat-shock protein; MARCKS, myristoylated alaminte-rich C kinase substrate; MHC, myosin heavy chain; NOS, nitric oxide synthase; PDE, phosphodiesterase; PFK, phosphofructokinase; PhK, phosphorylase kinase; sk-, smMLCK, skeletal muscle- and smooth muscle-myosin light chain kinase; VIP, vasoactive intestinal peptide.

Where a linker moiety is present, the length of the linker moiety is chosen to optimize the kinetics and specificity of responsiveness of the sensor polypeptide induced by the interaction of the chemical, biological, electrical or physiological parameter with the sensor polypeptide. The linker moiety should be long enough and flexible enough to allow the sensor polypeptide to freely interact and respond to a particular parameter. The linker moiety is, preferably, a peptide moiety. The preferred linker moiety is a peptide between about one and 30 amino acid residues in length, preferably between about two and 15 amino acid residues. One preferred linker moiety is a -Gly-Gly- linker. The linker moiety can include flexible spacer amino acid sequences, such as those known in single-chain antibody research. For example, the linker moiety can be GGGGS (GGGGS)$_n$ (SEQ ID NO:56), GKSSGSGSESKS (SEQ ID NO:57), GSTSGSGKSSEGKG (SEQ ID NO:58), GSTSGSGKS-SEGSGSTKG (SEQ ID NO:59), GSTSGSGKSSEGKG (SEQ ID NO:60), GSTSGSGKPGSGEGSTKG (SEQ ID NO:61), EGKSSGSGSESKEF (SEQ ID NO:62), GGTGEL (SEQ ID NO:1), FKTRHN (SEQ ID NO:2), or GGTGGS (SEQ ID NO:63). Linking moieties are described, for example, in Huston et al., Proc. Natl. Acad. Sci., USA 85:5879–5883 (1988), Whitlow et al., Protein Engineering 6:989–995 (1993), and Newton et al., Biochemistry 35:545–553 (1996).

Depending on the vector utilized, any of a number of suitable transcription and translation elements, including constitutive and inducible promoters, transcription enhancer elements, transcription terminators, etc. may be used in the expression vector (see, e.g., Bitter, et al., Meth. Enzymol. 153:516–544, 1987). Such elements are well known in the art.

In bacterial systems a number of expression vectors may be advantageously selected depending upon the intended use. For example, when large quantities of a protein of the invention is desired, vectors which direct the expression of high levels of chimeric protein products that are readily purified may be desirable. Those which are engineered to contain a cleavage site to aid in protein recovery are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Meth. Enzymol., Eds. Wu & Grossman, 31987, Academic Press NY, Vol. 153, pp. 516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y, Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith et al., *J. Virol.* 46:584, 1983; Smith, U.S. Pat. No. 4,215,051. Another alternative expression system includes plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent indicator or circularly permuted fluorescent protein.

By "transformation" is meant a permanent or transient genetic change induced in a cell following incorporation of new DNA (i.e. DNA exogenous to the cell). Where the cell is a mammalian cell, a permanent genetic change is generally achieved by introduction of the DNA into the genome of the cell.

By "transformed cell" is meant a cell into which (or into an ancestor of which has been introduced), by means of recombinant DNA techniques, a DNA molecule encoding a fluorescent indicator or circularly permuted fluorescent protein having an optically active polypeptide having operatively inserted therein a sensor polypeptide, or fragment thereof, which normally has two or more states, and which is affected by a chemical, biological, electrical or physiological parameter.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the chimeric polypeptide of the invention, and a second foreign DNA molecule encoding a selectable phenotype, such as the herpes simplex thymidine kinase gene. Another method is to use a eukaryotic viral vector, such as simian virus 40 (SV40) adenovirus, vaccinia virus, or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. Methods of stable transfer, meaning that the foreign DNA is continuously maintained in the host, are known in the art.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, secretion of the gene product should be used as host cells for the expression of fluorescent indicator. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a fluorescent indicator or circularly permuted fluorescent protein of the invention may be ligated to an adenovirus transcription/translation control complex, e.g., the late promoter and tripartite leader sequence. This nucleic acid sequence may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (see, for example, Logan & Shenk, *Proc. Natl. Acad. Sci. USA*, 81: 3655–3659, 1984). Alternatively, the vaccinia virus 7.5K promoter may be used (see, for example, Mackett et al., *Proc. Natl. Acad. Sci. USA*, 79: 7415–7419, 1982; Mackett et al., *J. Virol.* 49: 857–864, 1984; Panicali et al., *Proc. Natl. Acad. Sci. USA* 79: 4927–4931, 1982). Of particular interest are vectors based on bovine papilloma virus which have the ability to replicate as extrachromosomal elements (Sarver et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone and Mulligan, *Proc. Natl. Acad. Sci. USA*, 81:6349–6353, 1984). High level expression may also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with the cDNA encoding a fluorescent indicator or circularly permuted fluorescent protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler et al., Cell, 11: 223, 1977), hypoxanthine-guanine phosphoribosyltransferase (Szybalska and Szybalski, Proc. Natl. Acad. Sci. USA, 48:2026, 1962), and adenine phosphoribosyltransferase (Lowy et al., Cell, 22: 817, 1980) genes can be employed in tk⁻, hgprt⁻ or aprt⁻ cells respectively. Also, antimetabolite resistance can be used as the basis of selection for dhfr, which confers resistance to methotrexate (Wigler et al., Proc. Natl. Acad. Sci. USA, 77: 3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin (Santerre et al., Gene, 30: 147, 1984) genes. Recently, additional selectable genes have been described, namely trpB, which allows cells to utilize indole in place of tryptophan; hisD, which allows cells to utilize histinol in place of histidine (Hartman and Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue, In: *Current Communications in Molecular Biology*, Cold Spring Harbor Laboratory, ed., 1987).

A fluorescent indicator or circularly permuted fluorescent protein of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a chimeric protein of the invention. A primary advantage of the optically active polypeptides of the invention is that they are prepared by normal protein biosynthesis, thus avoiding organic synthesis and the requirement for customized unnatural amino acid analogs. The constructs can be expressed in *E. coli* in large scale for in vitro assays. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. Alternatively, the substrates can be expressed directly in a desired host cell for assays in situ.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

It should be understood that a nucleic acid sequence can also function as the concentration or available parameter in another embodiment of the invention. For example, a response may result from the interaction of a nucleic acid sequence with a sensor polypeptide comprising a DNA binding protein motif.

Screening Assays

The invention features a method for determining the presence of a chemical, biological, electrical or physiological parameter, by contacting the sample with a fluorescent indicator or circularly permuted fluorescent protein of the invention; exciting the indicator or protein; and measuring the amount of an optical property of the indicator or protein in the presence and absence of a parameter, such that a change in the optical property is indicative of an affect of the parameter on the indicator or protein. A series of standards, with known levels of activity, can be used to generate a standard curve. The optical event, such as intensity of fluorescence, that occurs following exposure of the sample to the fluorescent indicator or protein is measured, and the amount of the optical property is then compared to the standard curve. A standard, with a known level of activity, can be used to generate a standard curve, or to provide reference standards. The optical event, such as fluorescence, that occurs following exposure of the sample to the fluorescent indicator or protein is measured, and the amount of the optical property (e.g., fluorescence) is then compared to the standard in order to generate a relative measure of the affect of the sample on the fluorescent indicator.

In another embodiment, the invention features a method for determining if a cell exhibits an activity, which includes transfecting the cell with a nucleic acid encoding a fluorescent indicator or circularly permuted fluorescent protein of the invention; exciting the fluorescent indicator or circularly permuted fluorescent protein; and measuring the amount of an optical property in the presence of the activity and in the absence of the activity, such that a change in the optical property is indicative of activity. Typically, the optical property is calibrated against standard measurements to yield an absolute amount of protein activity.

The invention additionally, features methods for determining transient changes in a chemical, biological, electrical or physiological parameter, by contacting the sample with a fluorescent indicator or circularly permuted fluorescent protein of the invention and measuring a change in the optical property of the indicator over time.

It is understood that the cell containing a nucleic acid sequence encoding a fluorescent indicator or circularly permuted fluorescent protein of the invention can be used to co-transfect other genes of interest in order to determine the effect of the gene product of that gene on the cell or the sensor polypeptide of the fluorescent indicator or circularly permuted fluorescent protein. Therefore, a cell containing such a nucleic acid sequence is a composition provided by the present invention.

The invention can be used in screening assays to determine whether a compound (e.g., a drug, a chemical or a biologic) alters the activity of a particular protein, i.e., the sensor polypeptide (e.g., ligand binding to a receptor). In one embodiment, the assay is performed on a sample containing the chimeric protein in vitro. A sample containing a known amount of activity, such as an enzymatic activity, is mixed with a fluorescent indicator substrate of the invention, with the co-factors required for activity, and with a test compound. The amount of the enzyme activity in the sample is then determined by measuring the amount of an optical property, such as a fluorescent property, at least a first and second time after contact between the sample, the chimeric protein substrate of the invention, and any co-factors or components required to conduct the reaction, and the test compound. Then the amount of activity per mole of enzyme, for example, in the presence of the test compound is compared with the activity per mole of enzyme in the absence of the test compound. A difference indicates that the test compound alters the activity of the enzyme. In general a change in the optical parameter by any measurable amount between activity in the presence of the test compound as compared with the activity in the absence of the test compound, is indicative of activity.

In another embodiment, the ability of a compound to alter the activity of a particular protein (i.e., a sensor polypeptide) in vivo is determined. In an in vivo assay, cells transfected with a expression vector encoding a substrate of the invention are exposed to different amounts of the test compound, and the effect on the optical parameter, such as fluorescence, in each cell can be determined. Typically, the difference is calibrated against standard measurements to yield an absolute amount of protein activity. This provides a method for screening for compounds which affect cellular events (e.g., receptor-ligand binding, protein-protein interactions or protein kinase activation). In a given cell type, any measurable change between activity in the presence of the test compound as compared with the activity in the absence of the test compound, is indicative of activity.

The materials of the invention are ideally suited for a kit for determining the presence of an activity in a sample. Such a kit may contain a container containing a chimeric protein comprising an optically active polypeptide having operatively inserted therein a sensor polypeptide, or fragment thereof, which is affected by a change in a parameter or the environment, wherein optical properties of the sensor are altered in response to the change. In another embodiment, a kit of the invention contains an isolated nucleic acid sequence which encodes a chimeric protein comprising an optically active polypeptide having operatively inserted therein a sensor polypeptide, or fragment thereof, which is affected by a change in a parameter or the environment, wherein optical properties of the sensor are altered in response to the change. The nucleic acid sequence of the later kit may be contained in a host cell, preferably stably transfected. The cell could optionally be transiently transfected. Thus, the cell acts as an indicator kit in itself.

Transgenic Animals

In another embodiment, the present invention relates to transgenic animals that have cells that express an optically active polypeptide having operatively inserted therein a sensor polypeptide, or fragment thereof, which normally is capable of existing in two or more states, and which causes a change in the optical properties of the optically active polypeptide upon environmental conditions or parameters. Transgenic animals expressing high levels of the tagged transgene may be obtained, for example, by over-expression of the transgene with an enhanced promoter and/or with high copy numbers of the transgene. The transgenic animal may be heterozygous or homozygous for an ablated or disrupted endogenous indicator gene.

The "non-human animals" of the invention comprise any non-human animal having nucleic acid sequence which encodes a fluorescent indicator or circularly permuted fluorescent protein of the invention. Such non-human animals include vertebrates such as rodents, non-human primates, sheep, dog, cow, pig, amphibians, reptiles and fish. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 picoliters of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Viral infection can also be used to introduce transgene into a non-human animal (e.g., retroviral, adenoviral or any other RNA or DNA viral vectors). The developing non-human embryo can be cultured in vitro to the blastocyst stage. During this time, the blastomeres can be targets for retro viral infection (Jaenich, *Proc. Natl. Acad. Sci USA* 73:1260–1264, 1976). Efficient infection of the blastomeres is obtained by enzymatic treatment to remove the zona pellucida (Hogan, et al., in Manipulating the Mouse Embryo, Cold Spring Harbor Laboratory Press 1986.). The viral vector system used to introduce the transgene is typically a replication-defective retrovirus carrying the transgene (Jahner et al., *Proc. Natl. Acad. Sci. USA* 82:6927–6931, 1985; Van der Putten et al., *Proc. Natl. Acad. Sci. USA* 82:6148–6152, 1985). Transfection is easily and efficiently obtained by culturing the blastomeres on a monolayer of virus-producing cells (Van der Putten, supra, 1985; Stewart et al., *EMBO J.* 6:383–388, 1987). Alternatively, infection can be performed at a later stage. Virus or virus-producing cells can be injected into the blastocoele (Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (Jahner et al., supra).

A third type of target cell for transgene introduction is the embryonal stem cell (ES). ES cells are obtained from pre-implantation embryos cultured in vitro and fused with embryos (Evans et al., *Nature* 292:154–156, 1981; Bradley et al., *Nature* 309: 255–258, 1984; Gossler et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode the fluorescent indicator or circularly permuted fluorescent protein of the invention which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Methods For Identifying Insertion Sites

A number of methods for identifying insertion sites in fluorescent proteins, such as GFP, YFP, CFP, and dsRed are known in the art, including, for example, site directed mutagenesis, insertional mutagenesis, and deletional mutagenesis. Other methods, including that exemplified below and in the Examples, are known or easily ascertained by one skilled in the art (see, for example, Abedi et al, supra).

Sites in, for example, GFP mutants which can tolerate insertions of sensor polypeptides can be identified by generating mutant proteins by manipulating the DNA sequence such that a variety of different insertions are produced and screening the mutants by flow cytometry for mutants which retain fluorescence. Such insertions may include replacement of certain amino acids, as well as the addition of a new sequence without a corresponding deletion or replacement in the sequence of the fluorescent protein. Variants identified in this fashion reveal sites which can tolerate insertions while retaining fluorescence.

Additionally, circularly permutation techniques are also useful in identifying sites in fluorescent proteins which are capable of tolerating insertions while retain the ability to fluoresce. Such techniques include are exemplified herein as well as known to those of skill in the art (see, for example, Graf et al., *Proc. Natl. Acad. Sci USA,* 93:11591–11596 (1996), which is incorporated herein by reference).

In circular permutations, the original N-terminal and C-terminal amino acids of a fluorescent protein are engineered to be linked by a linker moiety. Such linker moieties include those described above, as well as other easily ascertain by one skilled in the art. This is typically performed at the nucleic acid level resulting in a polynucleotide sequence wherein the 5' codon encoding the N-terminal amino acid is linked to the 3' codon encoding the C-terminal amino acid, resulting in a circularized fluorescent protein nucleic acid sequence. The circularized sequence is then cleaved with a nuclease to create a linear polynucleotide sequence, the cleavage site corresponding to an amino acid in of the fluorescent protein. The cleavage of the circularized sequence is either random or specific depending on the desired product, nuclease, and desired sequence. The linearized polynucleotide, which contains sequence homologous to the starting fluorescent protein sequence, is cloned into an expression vector and expressed. The expressed polypeptide sequence is then screened, for example by flow cytometry, for polypeptides retaining the ability to fluoresce. Accordingly, polypeptides which retain the ability to fluorescence correspondingly, via identification of the cleavage site, identify amino acids which can tolerate insertions without destroying the ability of the fluorescent protein to fluoresce.

Methods of performing assays on fluorescent materials are well known in the art and are described, e.g., in Lakowicz, *Principles of Fluorescence Spectroscopy*, Plenum Press (1983); Herman, Resonance energy transfer microscopy, in: *Fluorescence Microscopy of Living Cells in Culture, Part B, Methods in Cell Biology*, vol. 30, ed. Taylor & Wang, San Diego: Academic Press (1989), pp. 219–243; Turro, *Modern Molecular Photochemistry*, Menlo Park: Benjamin/Cummings Publishing Col, Inc. (1978), pp. 296–361.

The following examples are intended to illustrate but not limit the invention.

EXAMPLE 1

Cells and Protein Purification:

Bacteria used in this study were BL21(DE3) Gold cells from Stratagene. Transformation was performed by electroporating cells suspended in 10% glycerol directly with a ligation mixture (0.1 cm cuvette, 12.5 kV/cm, 200 Ω, 25 uFd). For protein expression, cells were grown in LB broth containing 100 mg/L Ampicillin to an $OD_{600}$ of 0.6, at which time they were induced with 1 mM isopropylthiogalactoside. Bacteria were allowed to express recombinant protein for 6 hours at room temperature and then overnight at 4° C. The bacteria were then pelleted by centrifugation, resuspended in 50 mM Tris, 300 mM NaCl and lysed with a French Press. The bacterial lysates were centrifuged at 30,000×g for 30 minutes, and the supernatants were incubated with NiNTA resin (from Qiagen, used for purifying circularly permuted GFP and Calmodulin Insertions) or Cobalt Talon Resin (from Clontech, used for purifying zinc-finger inserts).

Cloning and Gene Construction:

Yellow GFP mutants (YFPs) with peptide insertions replacing Y145 were made by performing two separate polymerase chain reactions (PCRs). The first PCR amplified the N-terminal piece of YFP to include a 5' BamH1 site and 3' replacement of Y145 with the hexapeptide linker GGTGEL (SEQ ID NO: 1, coded for by DNA containing Kpn1 and Sac1 restriction sites for subsequent cloning). The second PCR amplified the C terminal piece of YFP to include the 5' linker (GGTGEL, SEQ ID NO: 1) replacing Y145 and a 3' EcoR1 site. These two PCR products were combined, amplified with N-terminal and C-terminal YFP primers to yield a full length cDNA containing the insertion. The full length cDNA was restricted with BamH1 and EcoR1, ligated and cloned into the BamH1 and EcoR1 sites of pRSET B (Invitrogen) to yield the plasmid pYFPins. Next, the cDNAs for Xenopus Calmodulin and the first zinc-finger motif from zif268 were amplified with PCR using primers containing 5' Kpn1 sites and 3' Sac1 sites and digested with Kpn1 and Sac1. Finally, insertions into YFPs were made by cloning cDNAs of inserted proteins in between the Kpn1 and Sac1 sites of pYFPins. (FIG. 1).

Figure 2A:
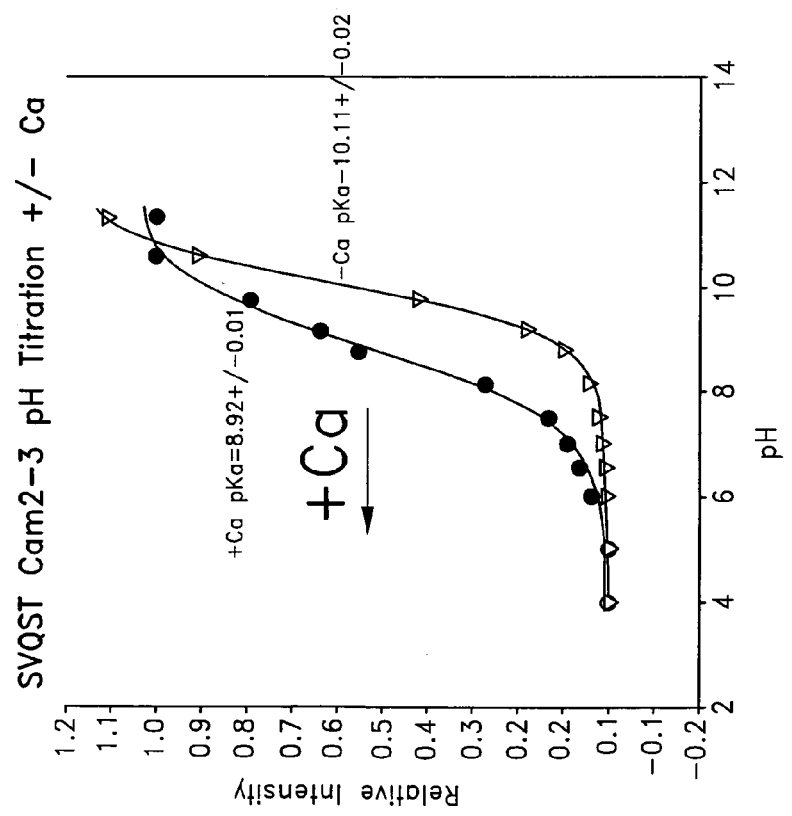
FIG. 2A shows pH effects on a calmodulin insertion indicator.

Protein Titrations:

Protein pH titrations were carried out in 125 mM KCl, 20 mM NaCl, 0.5 mM $CaCl_2$, 0.5 mM $MgCl_2$, and 50 mM buffer. Buffers were chosen to span a wide pH range, and included citrate (pH4–5), MES (pH 5.5–6.5), HEPES (pH 7–8.15), glycine (pH 8.8–10.7), and phosphate (pH 11.3–13.2). For each pH, a weakly buffered protein solution was mixed with an equal volume of the corresponding buffer solution and analyzed for total fluorescence in triplicate on a microplate fluorescence reader using a 482+/−10 nm excitation filter and a 532+/−14 nm emission filter (FIG. 2a).

Figure 3:
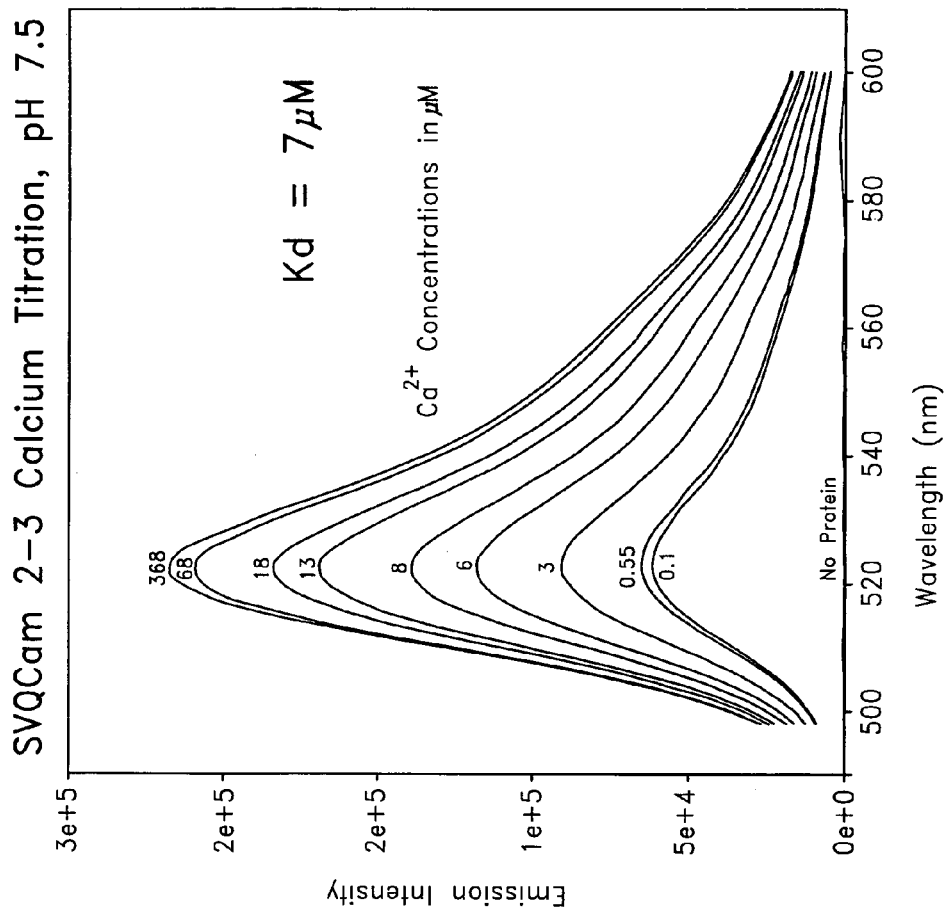
FIG. 3 further shows the effects of calcium concentration on fluorescence of a fluorescent indicator of the invention containing a sensor polypeptide of calmodulin.

Calcium titrations of YFP-Calmodulin insertion proteins were done in a cuvette in a fluorescence spectrometer in 100 mM KCl, 10 mM MOPS at pH7.5 (buffer was run through a Chelex column to remove traces of calcium). Small aliquots of $CaCl_2$ were added to this cuvette and a full fluorescence emission spectrum was taken after each addition. (FIG. 2b, FIG. 3).

Figure 4:
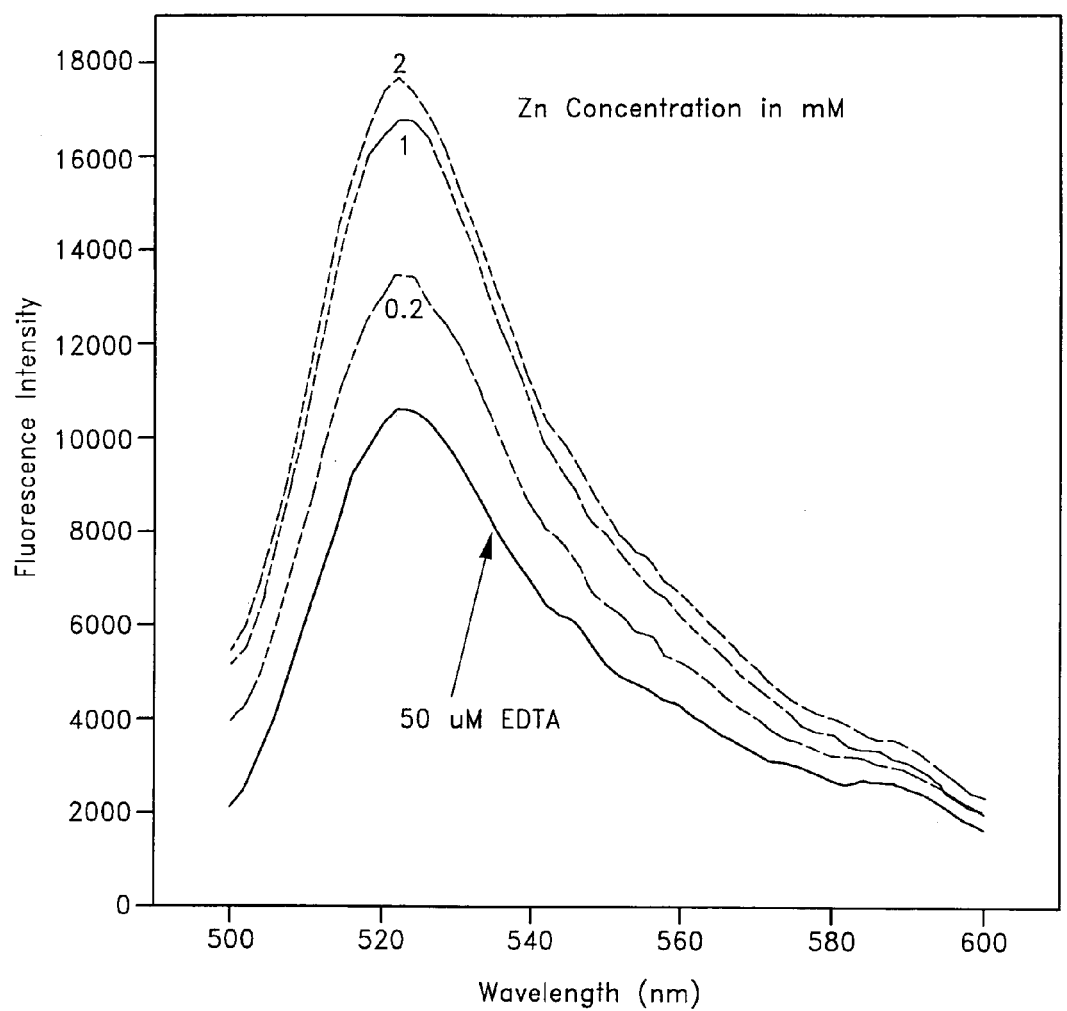
FIG. 4 show the effect of Zn concentration on fluorescence of a fluorescent indicator of the invention containing a sensor polypeptide of inserted Zif polypeptide.

Zinc titrations of YFP-zinc finger insertions were done in 50 mM MOPS, pH 7.0. A fluorescence emission spectrum was taken of the protein in buffer containing 50 uM EDTA, and then small aliquots of $ZnCl_2$ were added, and subsequent spectra were recorded (FIG. 4).

Titration curves were generated by averaging the three intensity values for each pH (for microplate data) or be integrating the total emission intensity (for full spectra), plotting these data versus analyte concentration, and fitting a sigmoidal curve to the data.

YFP containing calmodulin replacing Y145 show an pH-sensitive increase in fluorescence intensity on calcium binding, with an apparent Kd of fluorescence of 7 μM. The increase in fluorescence observed at constant pH reflects a shift of 1 pKa unit between the calcium-free and calcium-bound states of the protein, as observed in pH titrations done in the presence of or absence of free calcium (FIG. 2). In addition, the absorbance of this protein changes from a predominantly ultraviolet, non-fluorescent band to a predominantly blue, fluorescent band on calcium binding at constant pH. Since other studies suggest that the non-fluorescent, ultraviolet-absorbing band represents the protonated chromophore and the fluorescent, blue-absorbing band represents the deprotonated chromophore, these data show that calcium, binding alters the equilibrium between protonated and deprotonated chromophore states, i.e., changes the pKa of fluorescence.

YFPs containing a zinc-finger motif derived from zif268 also increase in fluorescence on binding zinc. The change in fluorescence for Zn-sensing YFPs is substantially less than that of Calmodulin-YFPs described above. First, as Zn finger motifs contain cysteine residues in close proximity, they can be prone to oxidation, which would prevent zinc binding. Second, the change of inserted proteins on substrate binding is responsible for the change in pKa and therefore the change in fluorescence. It could be possible that zinc-finger motifs adopt a non-optimal conformation on binding zinc, leaving the chromophore still vulnerable to protonation. Last, each of the three reasons listed above concerning the performance of YFP-Calmodulin Insertions could in principle also apply analogously to the zinc finger insertions. As stated above, the zinc-finger inserted YFP reported here is just a first generation prototype of what will likely become a powerful new class of indicators.

Figure 5:
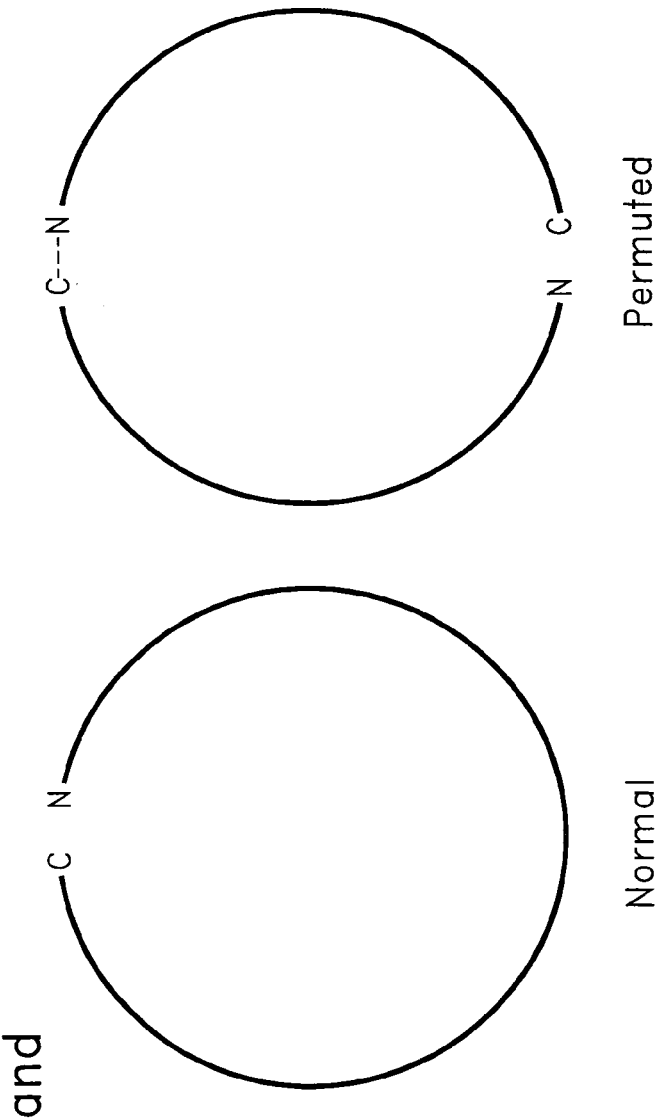
FIG. 5 shows the overall design of a circularly permuted polypeptide.

Circular Permutations:

Circular permutations of GFP mutants with a new N-terminus at Y145 were made by performing two separate PCRs. The first PCR amplified the C terminal piece of a GFP mutant (N-terminal in the final permuted gene) to have a 5' BamH1 site, the mutation Y145M, and a 3' hexapeptide linker (GGTGGS, SEQ ID NO: 63) containing a Kpn1 site. The second PCR amplified the N-terminal piece of the GFP mutant (C terminal in the final permuted gene) to have a 5' hexapeptide linker (GGTGGS, SEQ ID NO: 63) containing a Kpn1 site, and a 3' EcoR1 site. The first PCR product was digested with sequentially with BamH1 and Kpn1, the second PCR product was digested sequentially with EcoR1 and Kpn1, and the fragments were purified by agarose gel electrophoresis. The N- and C-terminal PCR fragments were then cloned in a three part ligation into the BamH1/EcoR1 sites of pRSET B. (See FIG. 5).

To construct a cameleon molecule containing circularly permuted CFP instead of CFP (called YC3.2), the circularly permuted CFP cDNA was amplified with PCR to contain an 5' BamH1 site and a 3' Sac1 site, digested with BamH1 and Sac1 and agarose gel purified. Then, a plasmid consisting of the YC3.1 cDNA cloned into the BamH1 and EcoR1 sites of pRSETB was digested with BamH1 and Sac1, and the 4.2 kb DNA fragment (YC3.1D CFP) was agarose gel purified. The circularly permuted CFP cDNA was then ligated to the YC3.1DCFP fragment, and the DNA was transformed into BL21(DE3) Gold cells as described above.

Random Circular Permutations were based on the method of Graf, et al. with major modifications because their original conditions were found to be unsuccessful when applied to GFP cDNAs. Through extensive testing, it was found that circular permutation required 1) reducing the concentration of DNA used when circularizing the gene from 300 μg/mL to 5 μg/mL, 2) increasing the amount of DNAse used to relinearize the fragment from 1 U/mg DNA to 100 U/mg DNA, 3) changing the temperature of DNAse incubation from 16 degrees to 22 degrees Celsius, and switching the DNA repair enzyme used from T4 to T7 DNA polymerase. Accordingly, the method of Graf et al., was substantially modified as follows. An expression vector for the random circular permutations was made by ligating an oligonucleotide containing a 5' EcoRV site and three downstream stop codons in each reading frame between the BamH1 and EcoR1 sites of pRSET B. This vector ("pRSET triple stop") was digested with EcoRV, treated with Alkaline Phosphatase, and purified by agarose gel electrophoresis.

Figure 6:
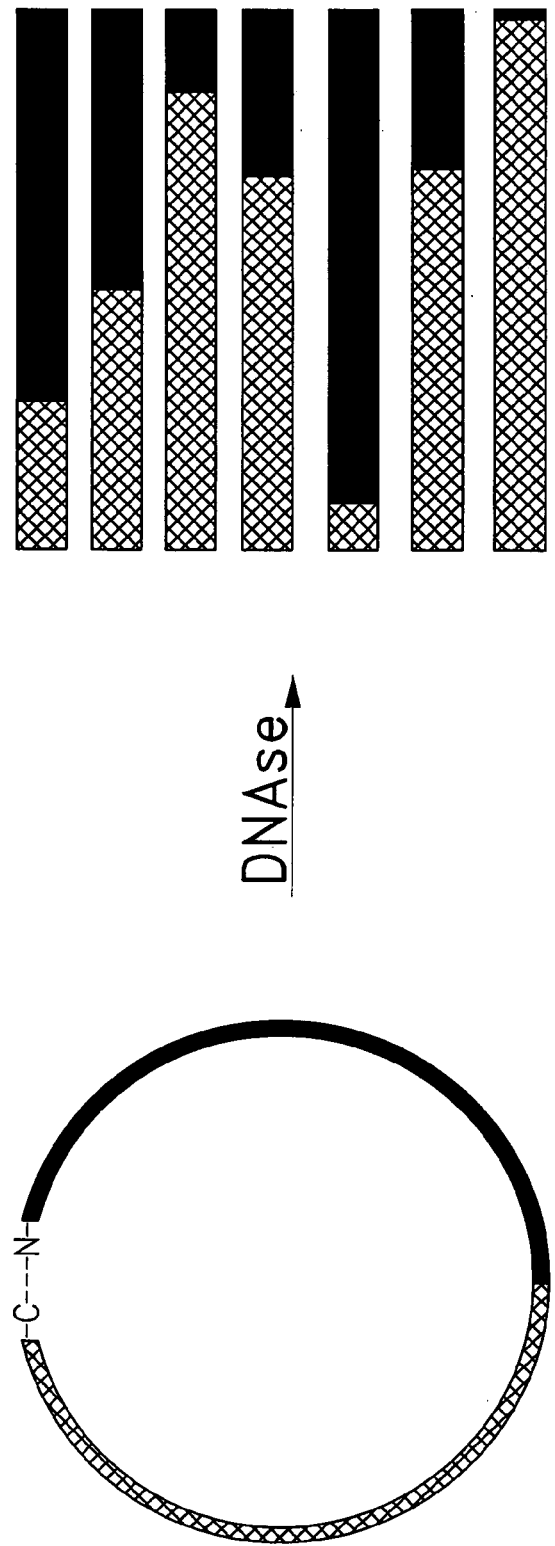
FIG. 6 shows the result of random digestion of a circularly permuted nucleic acid sequences.

To make a library of circular permutations, the circularly permuted GFP gene described above was amplified by PCR with primers that created a final PCR amplicon starting and ending at an Xho1 site (ctcgag) coding for residues L141 and E142. The PCR product was digested with Xho1 and cloned into the Xho1 site of a pBluescript™ plasmid. This plasmid was amplified in bacteria, purified with a Qiagen maxi-prep, digested with Xho1, and the ~730 bp fragment was agarose gel-purified to yield a linearized GFP gene. The linear fragment was circularized at a concentration of 5 μg/mL with 8000 U/mL T4 DNA ligase (New England Biolabs)

overnight at 16° C. After ethanol precipitation, the DNA was digested with DNAse (100 U/mg DNA, Pharmacia) for 15 minutes at room temperature in 50 mM Tris HCl, pH 7.5, and 1 mM $MnCl_2$. Digestion was stopped by phenol extraction, then subsequent phenol/chloroform/isoamyl alcohol and chloroform/isoamyl alcohol extractions. The DNA was ethanol precipitated, resuspended in 1× synthesis buffer (Stratagene) and incubated with T7 DNA polymerase (Stratagene) and T4 DNA ligase (Stratagene) at room temperature for 1 hour to repair DNA nicks and fill sticky ends (FIG. 6).

The linear, repaired, randomly permuted DNA library was purified by agarose gel electrophoresis, ligated blunt into the pRSET triple stop expression vector, and electro-transformed into BL21 bacteria.

LB/agar plates containing ampicillin usually displayed a few thousand colonies per plate and were screened by digital imaging of fluorescence. The plates were illuminated with a 150 W xenon arc lamp through a 450–490 nm bandpass filter and a pair of fiber optic light guides (Oriel Instruments) positioned to illuminate the top surface of the agar as evenly as possible. The emitted fluorescence was selected by a 510–550 nm bandpass filter and focused by a f/1.2 camera lens (Nikon) onto a cooled charge-coupled-device camera (Photometrics). Digital images from the camera were analyzed with Metafluor software (Universal Imaging Corp.). Out of approximately 25,000 bacterial colonies screened, about 200 became fluorescent after 24 hours at 4° C., and 144 of these were picked for plasmid minipreps and restriction analysis. All plasmid minipreps were digested with HindIII and KpnI to analyze the site of permuted termini (HindIII cuts 3' to the GFP gene in pRSETB, KpnI cuts at the linker between N and C termini of GFP). Clones which gave restriction fragments of ~750 bp or no visible fragments from 100–1000 bp were considered to be regenerations of nearly wild-type sequence and were not investigated further. Clones which gave restriction fragments between 100 bp and 1000 bp, but not 750 bp, were sequenced at their N-terminus and C-terminus to pinpoint the exact locations of new termini within the GFP sequence.

GFP forms a fluorescent circularly permuted protein when its native N-terminus and C-terminus are connected with the hexapeptide linker GGTGGS (SEQ ID NO: 63) and new N termini are formed at E142, Y143, Y145, H148, D155, H169, E172, D173, A227, or I229 (see Table 6). The permuted protein with the N terminus at Y145 was made and studied for the Cyan, Green, and Yellow mutants of GFP (cpCFP, cpGFP, cpYFP). In each case, the protein had a higher pKa of fluorescence than its native counterpart, although the fluorescence spectra were similar. This suggests that interrupting GFP and its mutants at Y145 generally increases the sensitivity of the chromophore to protonation, which is in agreement with the results obtained from the GFP insertions described above.

TABLE 6

Sequence Summary of Random Circular Permutations

| Starting Amino Acid | Ending Amino Acid |
|---|---|
| E142M | N144LSE |
| Y143N | N146LSE |
| Y143I | N144LSE |
| Y145I | N144 |
| H148I | N149LSE |
| H148I | K162SE |
| D155I | K156SE |
| H169H | N170LSE |

TABLE 6-continued

Sequence Summary of Random Circular Permutations

| Starting Amino Acid | Ending Amino Acid |
|---|---|
| H169I | N170LSE |
| E172M | I171DLSE |
| D173I | D173LSE |
| D173D | E172SE |
| A227A | A227I |
| I229I | I229I |

*Starting Amino Acid is the first amino acid for which is not coded for by the expression vector (which may also have been mutated), e.g. E142M means that the GFP starts at Position 142, but the glutamate residue has been changed to methionine by the cloning process.
*Ending Amino Acid is followed by the amino acid sequence added by the expression vector, e.g. N144LSE means that the GFP sequence ends with asparagine at position 144, but is appended by the C terminal tripeptide LSE. N144 means that the protein simply ends with asparagine at position 144 with no addition peptide.

Figure 7:
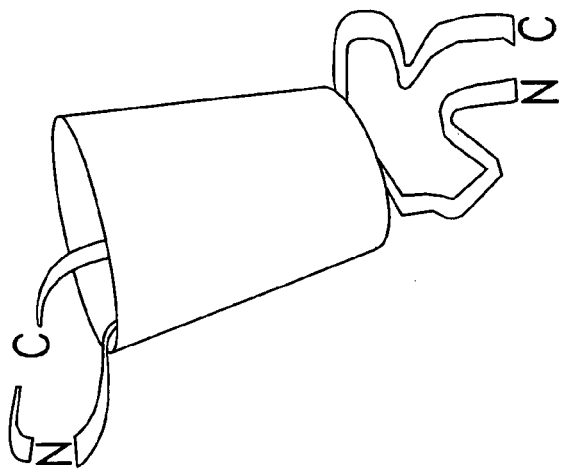
FIG. 7 shows insertions into GFP.
Figure 7:
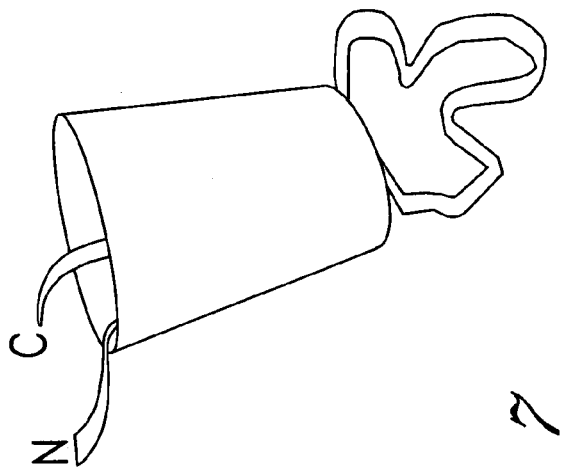
Figure 8:
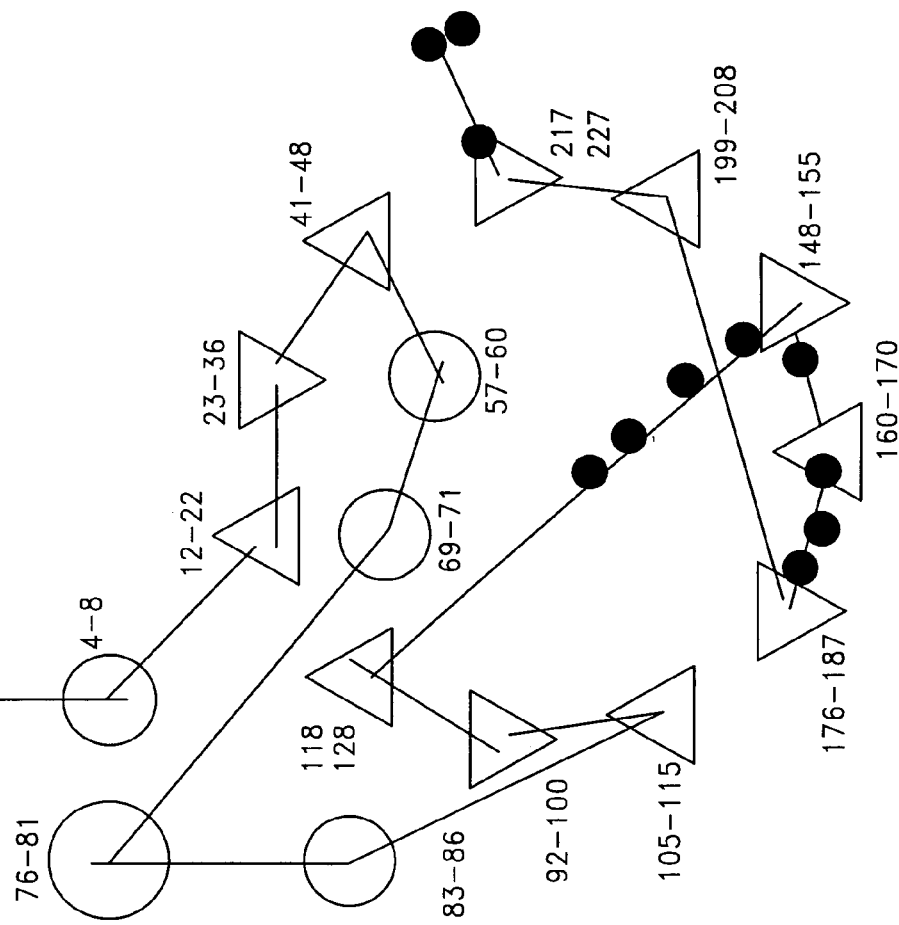
FIG. 8 shows a schematic diagram of potential insertional sites and sites for circular permutations in GFP.

To address cpCFP's orientation in space in fusion proteins, we constructed a cameleon molecule with cpCFP replacing CFP (YC3.2). With this modification, the FRET difference between calcium-free and calcium-bound states of cameleon changes dramatically compared to normal cameleons. This demonstrates that cpCFP maintains a different orientation in space than CFP, since other factors influencing FRET (inter-fluorophore distance and spectral overlap) have changed only very little. These data further suggest that the above list of possible cpGFP mutants represents a library of GFP mutants for use in FRET applications. Since most should have different orientations in space than regular GFP mutants, every FRET-based application of a GFP mutant that fails due to poor orientation could possibly be improved through use of cpGFP mutants. (FIG. 7).

One obvious use of cpGFP mutants relies purely on their increased pKa's. Subcellular pH can be measured with appropriately targeted non-permuted GFP mutants; however, the dynamic range of pH's over which non-permuted GFPs can measure is limited by the pKa's of available mutants. Since all circular permutants thus far investigated have higher pKas than their non-permuted counterparts, they theoretically extend the ability of GFPs to sense pH in more alkaline compartments, and could allow one to investigate relatively neutral compartments with blue-shifted mutants, which was previously not possible.

Another possible use of cpGFP mutants is in making novel insertions of GFP into other proteins for use as biosensors. GFP, because its termini are close in space, can be inserted into other proteins, but only rarely to date has it been shown to sense a conformational change in such a construct. When cpGFP mutants are inserted into a protein, they are topologically similar to the GFP insertion constructs described above, and they might reasonably be expected to have similar sensing properties as GFP insertions (FIG. 7).

GFP mutants with peptide insertions replacing Y145 were made by performing two separate polymerase chain reactions (PCRs). The first PCR amplified the N-terminal piece of GFP to include a 5' BAMH1 site and 3' replacement of Y145 wit the hexapeptide linker GGTGEL (SEQ ID NO: 1, coded for by DNA containing KpnI and SacI restriction sites for subsequent cloning). The second PCR amplified the C-terminal piece of GFP to include the 5' linker (GGTGEL, SEQ ID NO: 1) replacing Y145 and a 3' EcoR1 site. These two PCR products were combined, amplified with N-terminal and C-terminal GFP primers to yield a full length fragment, restricted with BamH1 and EcoR1, ligated and cloned into the BamH1 and EcoR1 sites of pRSETB (Invitrogen). Subsequent insertions into this GFP were made by cloning nucleic acid sequences of a desired binding moiety in between the Kpn1 and SacI sites of this plasmid. Any sensor polypeptide can be inserted into a fluorescence protein (e.g., GFP, YFP, or CFP) by analogy to the method described above and put in a cell by introducing the cDNA coding for the protein into the cell in a vector that directs protein production. The indicator is then visualized using a fluorescence method.

EXAMPLE 2

This example provides a characterization of citrine, which is a YFP mutant (S65G/V68L/Q69M/S72A/T203Y), and dsRed (Heikal et al., *Proc. Natl. Acad. Sci., USA* 97:11996–12001 (2000), which is incorporated herein by reference).

A. Methods

Citrine was created with the QuickChange™ Site-Directed Mutagenesis Kit (Stratagene) by using the cDNA coding for the mutant 10C Q69K (Miyawaki et al., *Proc. Natl. Acad. Sci., USA* 96:2135–2140 (1999), which is incorporated herein by reference). Both dsRed (CLONTECH) and Citrine DNAs were cloned into the vector pRSETB (Invitrogen). Proteins were produced in JM109 (DE3) *Escherichia coli* (Baird et al., supra, 2000), purified by nickel chelate chromatography on NiNTA-agarose, dialyzed against 10 mM Tris-HCl, pH 7.5. They were stored at 4° C. before dilution into buffers at various pH for spectroscopy.

One-photon absorption spectra were measured with a single-beam HP-8451-A Diode Array Spectrometer, whereas the fluorescence spectra were recorded by using a PTI-QM-1 fluorimeter. For fluorescence correlation spectroscopy (FCS) measurements, Ar⁺-laser lines (488 or 514 nm) were selected by interference filters, reflected by a dichroic mirror, and focused by a 1.15 numerical aperture/40× water immersion objective onto the sample, held in a 200 ml-deep well glass slide.

Fluorescence was collected through the same objective, a dichroic mirror, and 525+/−50 nm (citrine) or 580+/−50 nm (dsRed) filters and focused by a 150-mm achromat into an optical fiber (50 mm diameter). The fluorescence signal was detected by a fiber-coupled avalanche photodiode (APD; SPCM-AQ-141-FC; EG & G, Salem, Mass.). The APD signal was processed by using a correlator card (ALV5000; ALV Laser, Germany), and correlation curves were fitted by using the following function (Schwille et al., supra, 2000):

$$G(\tau) = \frac{1}{N}\left(\frac{1}{1+\tau/\tau_D}\right)\left(\frac{1}{1+\tau/\omega^2\tau_D}\right)^{0.5} \prod_{i=1}^{m} \frac{1}{(1-f_i)}(1-f_i+f_i e^{-\tau/\tau_1}), \quad [1]$$

where N denotes the mean number of fluorescent molecules diffusing within the excitation volume. Diffusion kinetics in the Gaussian intensity profile (with axial-to-lateral dimension ratio v) are characterized by the factors containing diffusion time ($\tau_D$). The exponential decay terms describe the dynamics of m independent transition pathways between states of different spectroscopic properties, e.g., protonated and deprotonated states (Haupts et al., supra, 1998) or generally photoconversion between any bright and dark states including singlet/triplet (Widengren et al., *J. Phys. Chem.* 99:13368–13379 1995)). The fraction fi of molecules residing in a dark state for ti duration can be determined from the measurements; for diffusion alone, fi 5 0.

Time- and polarization-resolved fluorescence measurements were carried out by using a TCSPC setup consisting of IR-femtosecond laser pulses from a mode-locked Ti/Sapphire laser pulse-picked (4 MHz) frequency doubled to generate 490 nm and 405 nm got: wavelengths, and then focused into the sample (≈5 µM) in a 3×3-mm quartz cell. Dispersed right-angle fluorescence was imaged onto a microchannel plate mounted at the exit slit of a spectrometer and then amplified before single photons were detected during each start/stop cycle (O'Connor and Phillips, supra, 1984) by using a PC-controlled single-photon-counting module (SPC-430; Becker and Hickl, Berlin). The instrument response (FWHM≈60 ps) was measured routinely and used for deconvolution in a nonlinear least-squares fitting routine based on Marquardt's algorithm (O'Connor and Phillips, supra, 1984). Magic-angle (54.7°) detection was used to eliminate the rotational effects on the measured fluorescence decays. For the time-resolved fluorescence anisotropy (O'Connor and Phillips, supra, 1984, Lakowicz, in Principles of Fluorescence Spectroscopy (Kluwer 1999)), parallel and perpendicular fluorescence polarization was selected by using a Glan-Thompson prism mounted at the entrance slit of the spectrometer. The G-factor, which accounts for the polarization sensitivity of the spectrometer grating as a function of wavelength, was estimated experimentally (O'Connor and Phillips, supra, 1984, Lakowicz, supra, 1999).

B. Results

Spectroscopy

One-photon and Two-photon (2P) Steady-state Spectra

Figure 9:
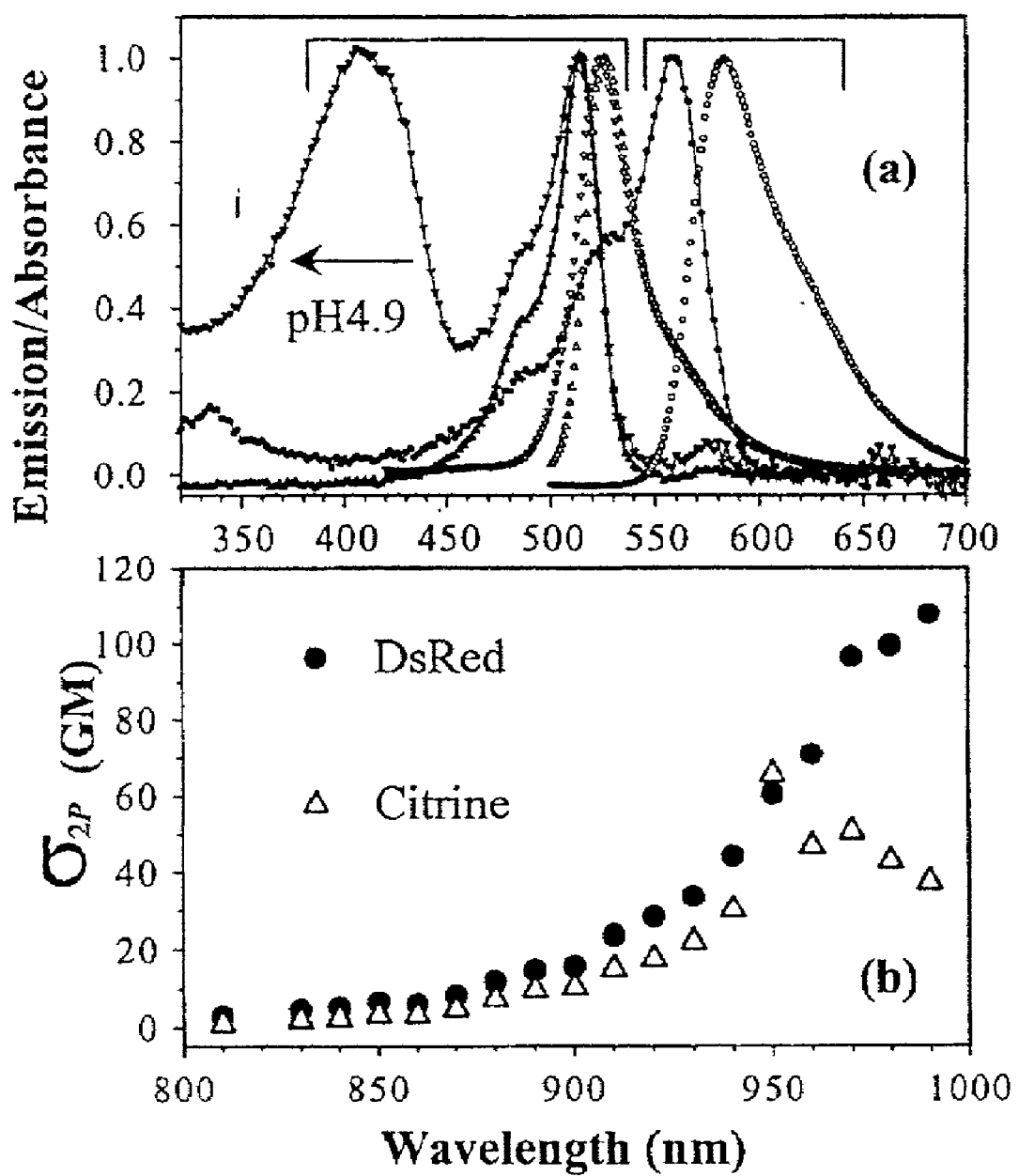
FIGS. 9A to 9B show absorption and emission spectra of dsRed and Citrine

In agreement with Baird et al. (supra, 2000), dsRed (pH 9.0) showed a strong absorption at 559 nm with two minor shoulders at 526 and 490 nm (FIG. 9). The fluorescence emission peaked around 583 nm and, therefore, can be useful for cellular studies to enable avoidance of the cellular autofluorescence complications. Mutations of wild-type (wt) GFP aimed to enhance and red shift the anionic (deprotonated) state transition (strongly fluorescent) while minimizing the neutral (protonated) state population (weakly fluorescent; Tsien, supra, 1998). Amino acid substitutions Ser-653Gly (e.g., citrine, T203Y, T203F) and Ser-653Thr (e.g., EGFP, S65T) destabilized the neutral state of the chromophore by reducing solvation of the anionic form of the Glu-222 side chain (Brejc et al., *Proc. Natl. Acad. Sci., USA* 94:2306–2311 (1977)). However, the neutral ($S^N_0$) ground state population of the essentially neutral chromophore can be enhanced by the environmental pH through proton exchange with the buffer to form an overall neutral molecular system as shown in EGFP (Haupts et al., supra, 1998), T203Y, and T203F (Schwille et al., supra, 2000).

Comparative FCS studies (Haupts et al., supra, 1998) on EGFP and Y66W confirmed that the hydroxyl group in Y66 is the site for the external proton localization. Substitution of Thr-203 amino acid in YFPs (e.g., T203Y, T203F, citrine) was responsible for the bathochromic shift of the anionic state transition by at electron stacking (Tsien, supra, 1998) with the Y66 moiety. The neutral state absorption (≈12 nm) in citrine is enhanced at low pH, whereas the main absorption band at 514 nm is reduced by a factor of about 3.7 (FIG. 9). This red shift (≈17 nm) of the neutral absorption, compared withz ≈395-nm absorption in other GFP mutants (Tsien, supra, 1998), suggests a small modification of the immediate surroundings of the neutral chromophore. The blue wing of the main emission band (524 nm) is also affected at low pH, possibly because of the neutral excited $S^N_1$-state emission. Comparison with the analogous mutant, T203Y (S65GyS72AyT203Y) (Schwille et al., supra, 2000; Dickson et al., supra, 1997), suggests that Q69M might play an important role in altering the spectroscopy and pKa (see below) in neutral citrine, based on the decreased polarity of Met compared with Gln.

2P-excitation cross-section ($\sigma_{2P}$) spectra of dsRed and citrine (FIG. 9B) were measured at pH 9.0 over the range 730–990 nm by using fluorescein and rhodamine B (Xu et al., *Bioimaging* 4:198–207 (1996)) as references. Extinction coefficients $\epsilon$=75,000 (dsRed) and 80,000 (citrine) cm$^{-1}$ M$^{-1}$ plus fluorescence quantum yield Q$_f$=0.75 were used. The $\sigma_{2P}$ value ($\approx$100 GM at 990 nm) for dsRed was comparable with EGFP ($\approx$113 GM in pH 11) and may have even higher $\sigma_{2P}$ as the excitation wavelength ($\lambda_{ex}$) approaches twice the one-photon-absorption peak of 558 nm. At 970 nm, a $\sigma_{2P}\approx$50 GM was observed for citrine. A large $\sigma_{2P}$ is desirable for cellular imaging by using multiphoton fluorescence microscopy (Denk et al., supra, 1995, see pages 445–458), and the maxima are located well above 800 nm, which minimizes photodamage in biological preparations and maximizes penetration depth for deep-tissue imaging.

Dynamics: Fluorescence Flicker

Light-driven Flicker

Figure 10:
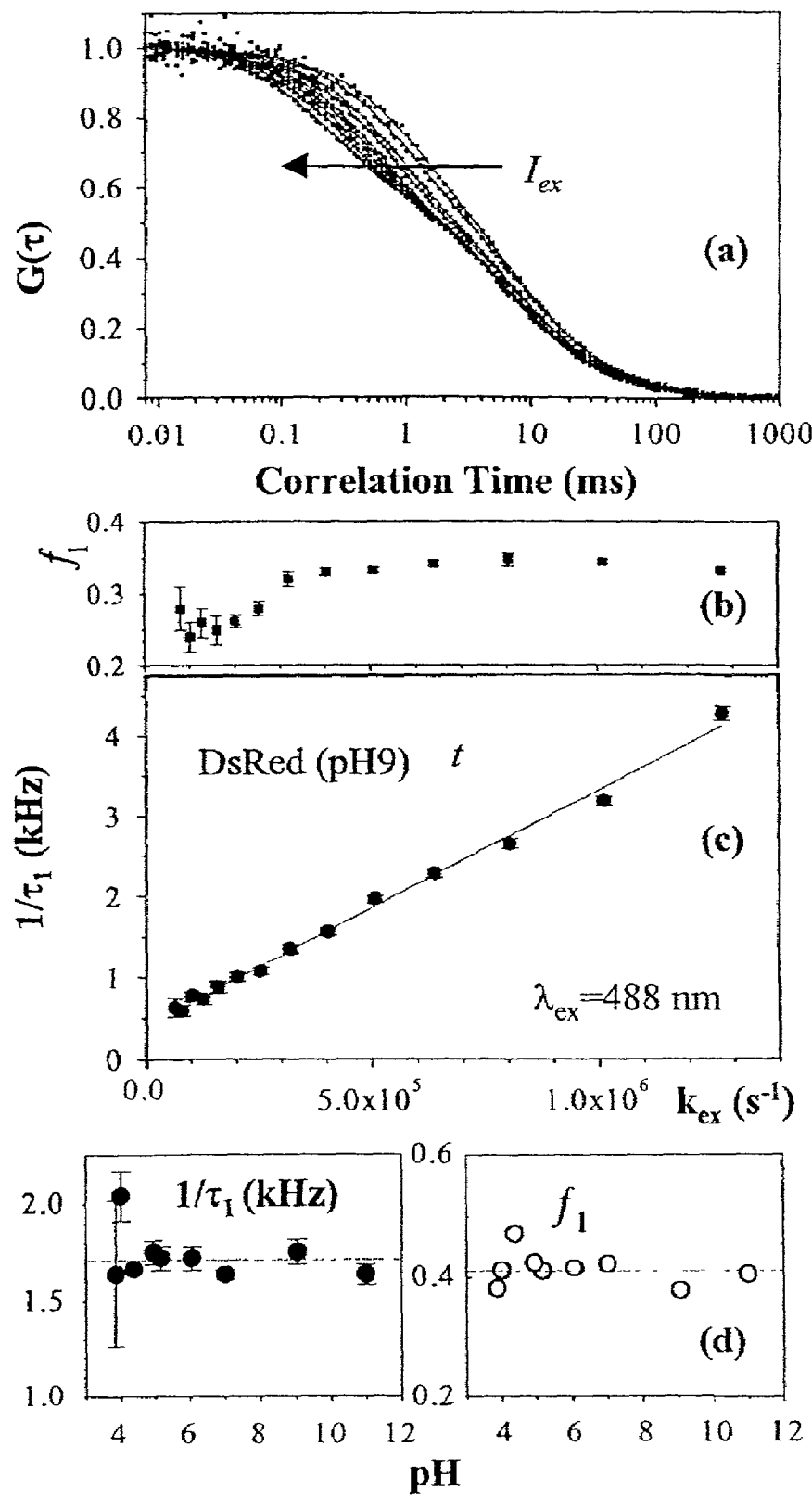
FIGS. 10A to 10D show fluorescence correlation spectra of dsRed.

In addition to diffusion, the FCS correlation curves of dsRed (pH 9, FIG. 10A) vary with illumination intensity at 488 nm, indicating the presence of intramolecular photoconversion dynamics on an approximately 0.04 to 1-ms time scale in addition to diffusion. At low intensity, the measured correlation curves are best described by one exponential term with time constant $\tau_1$ and fraction $f_1$ in addition to diffusion (Eq. 1). The flicker rate ($\tau_1^{-1}$) increases linearly with the excitation rate $k_{ex}$) at a photoconversion quantum yield $\Phi_1$=$\Delta\tau_1^{-1}$/$k_{ex}$=2.9+/−0.2×10$^{-3}$ (FIG. 10C). The fraction $f_1$=0.3+/−0.06 was nearly independent of intensity, implying that photoconversion occurs in both directions (dark$\leftrightarrows$bright). However, f1 appears to decrease at very low intensity, indicating spontaneous transitions from the dark to the anionic ground state at approximately 400+/−30 Hz as suggested by the extrapolation of $\tau_1^{-1}$ as $k_{ex}\to$0. At $k_{ex}$=514 nm, $f_1$=0.42+/−0.06 and $\Phi_1$=1.3+/−0.3×10$^{-3}$, suggesting that the quantum yield for the reverse photo-conversion is $k_{ex}$ dependent. Above the apparent saturation ($I_{Sat}\approx$17 kWcm$^{-2}$), the flicker rates become nonlinear in the excitation rate without reaching a limiting value, and an additional exponential term is required as expected for singlet-triplet intersystem crossing. Similarly, citrine (pH 9) also flickers by photoconversion generating a dark fraction (0.37+/−0.02) with $\Phi_1$=3.5+/−0.6×10$^{-3}$ under 488 nm illumination. Both the flicker fraction and quantum yield agree with FCS studies on T203Y (Schwille et al., supra, 2000). The flicker fraction and rates of dsRed were independent of pH (FIG. 10D).

Fluorescence blinking of immobilized individual T203Y and T203F mutants with a time scale of a few seconds has been observed by using wide-field microscopy, with on/off switching attributed to a slow photoconversion between the anionic, intermediate, and neutral states of the chromophore (Dickson et al., supra, 1997). The fluorescence recovery is thought to occur via an internal proton transfer on the excited-state potential energy surface (PES; see, for example, Tsien, supra, 1998; Chattoraj et al., *Proc. Natl. Acad. Sci., USA* 93:8362–8367 (1996)) after 405 nm irradiation. Fast flicker of these mutants was later discovered and studied by using FCS (Schwille et al., supra, 2000). In dsRed and citrine, similar excitation-driven fluorescence flicker observed in this report by using FCS can also be attributed to a reversible internal proton transfer reaction between the anionic $S^A_0$ and intermediate $S^I_0$ (and possibly the neutral $S^N_0$) ground states, on the basis of the energetics of the transitions. The observed increase of the photoconversion rate with excitation rate $k_{ex}$ shows that the excited-state PES serves as the gateway for the reported flicker process. After the anionic state $S^A_0 \to S^A_1$ transition, the excited state relaxes radiatively (i.e., large Q$_f$), and different vibrational levels on the $S^A_0$-state PES will be populated. However, there is a small probability ($\Phi_1\approx$10$^{-3}$) that the chromophore photoconverts to virtually dark $S^I_0$ and $S^N_0$ states according to our excited-state dynamics (see TCSPC results below). The dark-to-bright state photoconversion transition appears to follow the reverse route, because $f_1$ remains fairly $k_{ex}$ independent.

pH-Dependent Flicker

Figure 11:
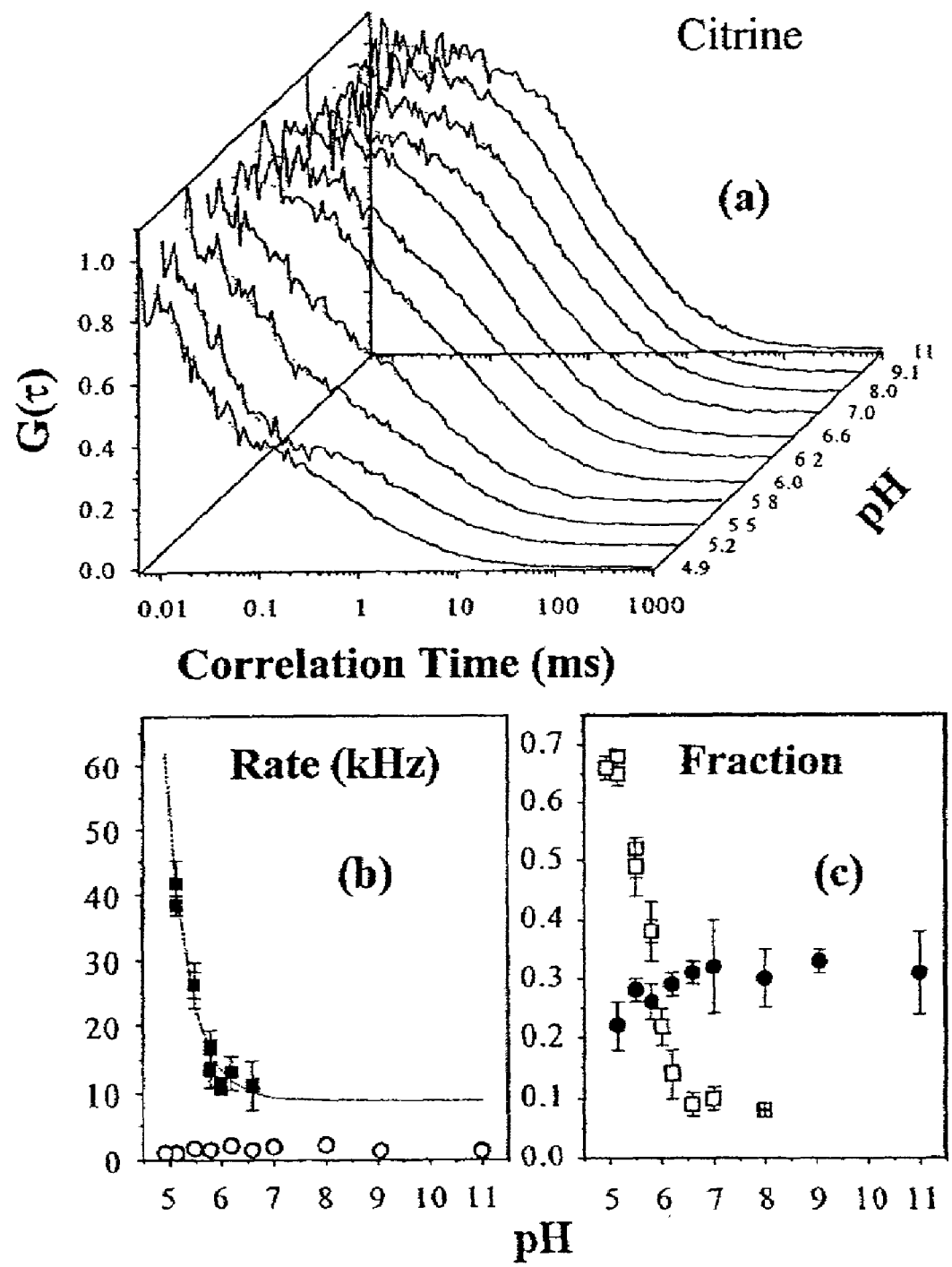
FIGS. 11A to 11C show that FCS measurements of citrine, as a function of pH, reveal an external protonation process. The correlation functions (FIG. 11A), rate constants (■.

The fluorescence autocorrelation of dsRed, excited at 488 nm, was insensitive to the environmental pH over the range 3.9–11 (FIG. 10D). Thus, the correlation functions at 3.9$\leq$pH$\leq$11 are identical to the right-hand curve in FIG. 10A. These results indicate the absence of external proton binding kinetics in dsRed in contrast with EGFP (Haupts et al., supra, 1998), T203Y (Schwille et al., supra, 2000), and citrine (FIG. 11). The fluorescence autocorrelation of citrine at low pH required two exponential terms in addition to diffusion, implying the existence of two routes for the bright-to-dark state flicker: pH-dependent proton binding and excitation-driven photoconversion transitions. For a reversible proton-binding reaction, the flicker rate $\tau_2^{-1}\approx k_+$[H$^+$]+k$_-$ and fraction $f_2$=K$_e$[H$^+$](1+K$_e$[H$^+$])$^{-1}$ with equilibrium constant K$_e$=k$_+$/k$_-$, where k$_+$ is the protonation and k$_-$ is the deprotonation rate constant (Elson and Magde, supra, 1974; Dickson et al., supra, 1997). The estimated rates are k$_+$=4.5+/−0.4×10$^9$ M$^{-1}$sec$^{-1}$, and k$_-$=9+/−1×10$^3$ sec$^{-1}$ with pKa=log(k$_+$/k$_-$)=5.7+/−0.1 for citrine with an estimated standard free energy $\Delta_r$G$^0$=32.7+/−0.5 kJ/mol at room temperature. These parameters differ slightly from T203Y (Schwille et al., supra, 2000), where k$_+$=1.4×10$^9$ M$^{-1}$sec$^{-1}$, and k$_-\approx$7×10$^3$ sec$^{-1}$, pKa$\approx$5.3, and $\Delta_r$G$^0$=30.4 kJ/mol. The concentration of halide or nitrate ions are known to affect pKa of YFPs that contain Thr203$\to$Tyr; for example, the pKa of T203Y ranges from 5.2 to 7.0 over a chloride concentration range of 0–400 mM (Wachter and Remington, Curr. Biol 9:R628–R629 (1999)). Therefore, changes in chloride ion concentration may complicate the use of YFPs as pH indicators in living cells. Citrine represents an alternative pH indicator, which is insensitive to the chloride concentration and exhibits desirable spectroscopic features with long absorption/emission wavelength. The pH-independent flicker rate $\tau_1^{-1}$=1.6+/−0.4×10$^3$ sec$^{-1}$ and the dark fraction $f_1$=0.30+/−0.06 (FIG. 11) represent the light-driven photoconversion process in citrine. These photo-conversion processes do require intensity control in the applications of these fluorescent proteins as pH indicators.

First Excited Electronic-State Dynamics

The first excited electronic $S_1$-state fluorescence relaxation in most fluorophores takes place on fast time scales (10$^{-11}$ to 10$^{-8}$ sec), compared with the diffusion and flicker dynamics (10$^{-6}$ to 10$^{-1}$ sec) observed with FCS, and provides a sensitive probe of the molecular environment. The excitation-energy dependence of these dynamics provides insights into the molecular states that underlie the fluorescence emission in complex systems such as dsRed and citrine. Here we present the fluorescence dynamics of the anionic (low-energy)- and neutral (high-energy)-state transitions of the chromophores by using TCSPC.

Low-Energy Transition

Figure 12:
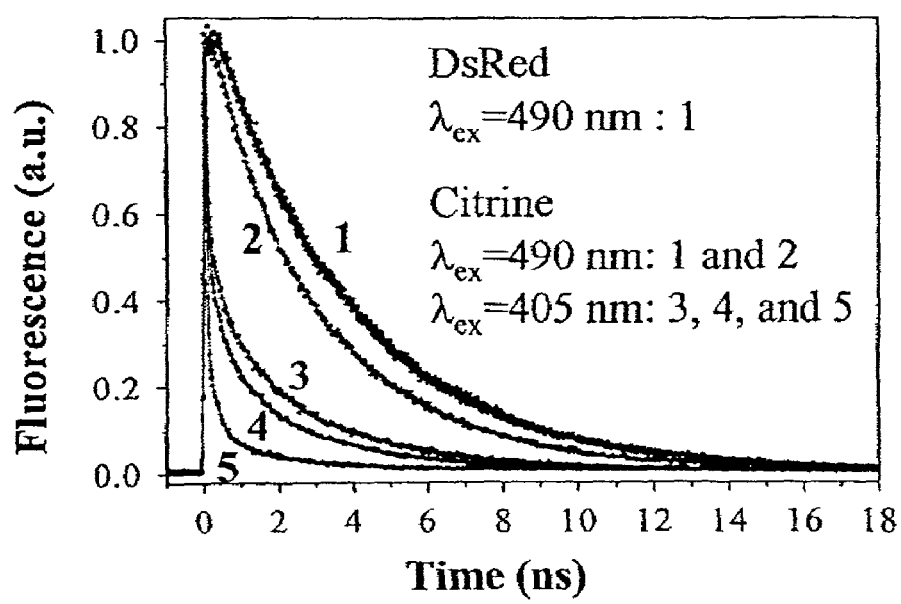
FIG. 12 shows the first excited electronic-state fluorescence decays of dsRed and citrine by using TCSPC. First excited anionic ($S^A_1$, $\lambda_{ex}$=490 nm), and neutral ($S^A_1$, $\lambda_{ex}$=405 nm) state dynamics of dsRed and citrine. After 490 nm excitation of dsRed (pH 9), the fluorescence decays as a single exponential with $\tau_f$=3.67 ns and $\chi^2$=1.08 (curve 1), whereas $\tau_f$=3.61 ns and $\chi^2$=1.06 (curve 1) for citrine. Unlike dsRed, citrine fluorescence exhibits a biexponential decay (curve 2: $\tau_{f1}$=3.31 ns, $\tau_{f2}$=880 ps, amplitude ratio $a_2/a_1 \approx 0.26$, and $\chi^2$=1.06) at pH 4.9. The fluorescence decays (curves 3–5), following the $S^N_0 \rightarrow S^N_1$ transition in citrine (pH 4.9) by using 405 nm, are also shown as function of detection wavelength: $\lambda_{ex}$=460 nm (curve 5: $\tau_{f1}$=524 ps, $\tau_{f2}$=268 ps, $\tau_{f3}$=2.11 ns, amplitude ratios $a_2/a_1 \approx 0.11$, $a_3/a_1 \approx 0.04$, and $\chi^2$=1.06); $\lambda_{ex}$=500 nm (curve 4: $\tau_{f1}$=51 ps, $\tau_{f2}$=452 ps, $\tau_{f3}$=2.63 ns, $a_2/a_1 \approx 0.16$, $a_3/a_1 \approx 0.06$, and $\chi^2$=1.21); and $\lambda_{ex}$=520 nm (curve 3: $\lambda_{f1}$=54 ps, $\lambda_{f2}$=712 ps, $\lambda_{f3}$=3.12 ns, $a_2/a_1 \approx 0.19$, $a_3/a_1 \approx 0.16$, and $\chi^2$=1.28).
Figure 13:
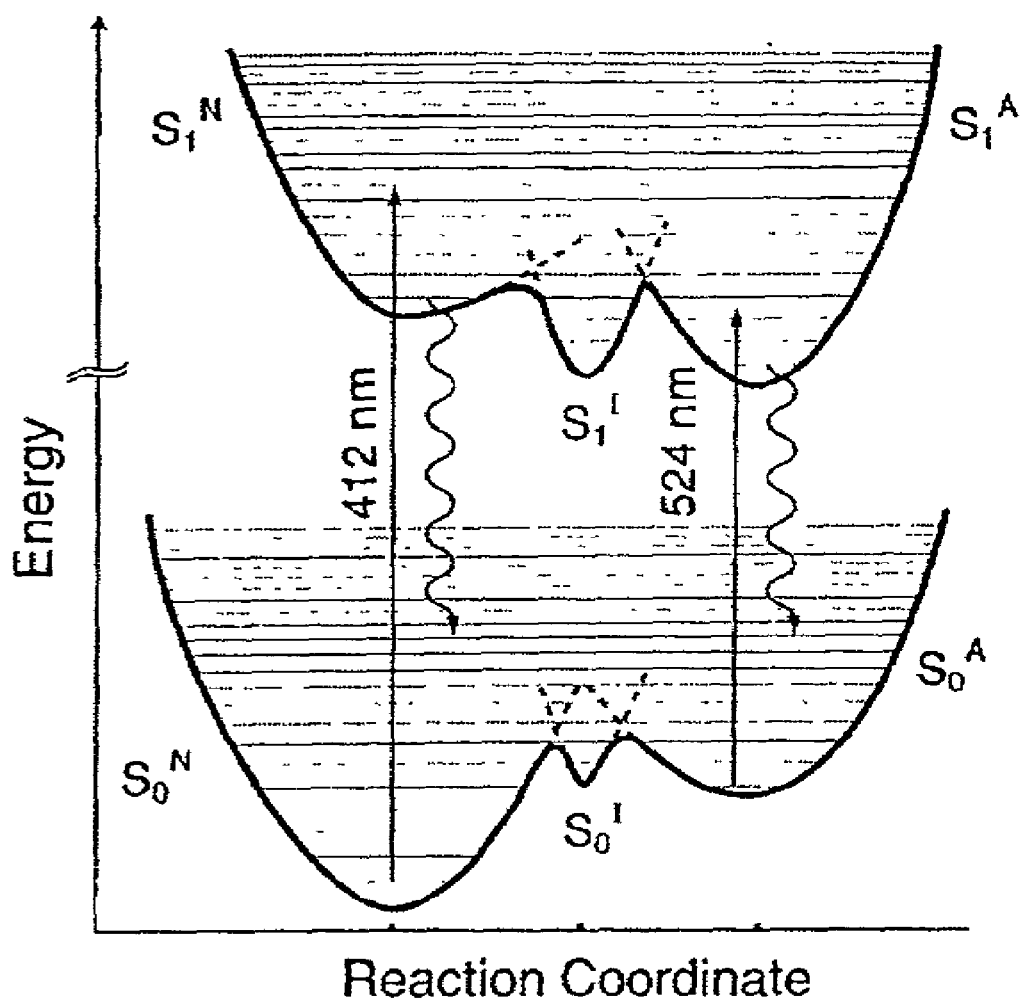
FIG. 13 shows a schematic PES of the anionic ($S^A_0 \rightarrow S^A_1$) and neutral ($S^N_0 \rightarrow S^N_1$) and intermediate ($S^I_0 \rightarrow S^I_1$) state transitions in citrine. The reaction coordinate is presumably internal proton transfer between the chromophore, particularly Y66, and the immediate hydrogen bond network. The crossing point between PES's along the reaction coordinate forms a barrier whose height and width depend on pH and mutation type/site. The anionic $S^A_1$ state of citrine decays via fluorescence at a rate $\tau_f^{-1}$ and, consequently, a range of vibrational levels on the $S^A_0$-PES will be populated followed by a probability for nonradiative vibrational relaxation to the bottom of the $S^A_0$, $S^I_0$, and $S^N_0$ PES's depending on the barriers. Fluorescence decays of the neutral $S^N_1$ state of citrine chromophore suggest an efficient nonradiative channel (e.g., intramolecular excited-state proton transfer) that competes with fluorescence. It is most likely that the $S_1$ state in dsRed has anionic character analogous to most GFP mutants, and the neutral state $S^N_0 \rightarrow S^N_1$ transition probability is negligible.

The $S_1$-state fluorescence decays of 490 nm-excited dsRed with a single exponential fit with 3.65+/−0.08 nanosecond (ns) time constant, independent of pH (4.4–9.0), indicating the existence of only one fluorescent excited state (FIG. 12). Electronic states in the low-energy transition of wt GFP (Tsien, supra, 1998; Lossau et al., *Chem. Phys.* 213:1–16 (1996; Kummer et al., *Chem. Phys.* 237:183–193 (1998)) and several of its mutants including EGFP have an anionic character with $S^A_1$ lifetime ≈2.9–3.7 ns. Theoretical studies and mass spectroscopy of dsRed (Baird et al., supra, 2000; Gross et al., supra, 2000) predict the main features of the embodied chromophore in GFP are preserved in dsRed, as suggested by sequence comparison between dsRed and wt GFP (Matz et al., *Nat. Biotechnol.* 17:969–973 (1999)). Therefore, it is most likely that the electronic transition in dsRed, with maximum absorption at 553 nm, is anionic ($S^A_0 \rightarrow S^A_1$; FIG. 13), analogous to most GFP mutants.

In citrine and other YFPs, the phenolate anion is stacked with a π electron system causing a red shift of the anionic $S^A_0 \rightarrow S^A_1$ transition (FIG. 13). Consequently, the anionic excited state in citrine is stabilized according to the energetics and the $S^A_1$ lifetime ($\tau_f$=3.61+/−0.03 ns at pH 9, FIG. 12) relative to wt GFP with a $\tau_f \approx 3.3$ ns. However, an additional $\tau_{f2} \approx 880$ ps decay component was observed at pH 4.9 with amplitude ratio $a_2/a_1 \approx 0.26$. Because the red tail of protonated neutral state absorption (FIG. 9A) at 490 nm is much less than 0.2, the 880 ps decay component likely can be attributed to the intermediate excited $S^I_1$ state of citrine. Furthermore, the slow component ($\tau_1 \approx 3.3$ ns), FIG. 12, slightly shorter than the $S^A_1$-state lifetime, indicates that the barrier height between the $S^A_1$ and the $S^I_1$ state is reduced in low pH environment and facilitating barrier crossing as a nonradiative pathway. In other words, the anionic, intermediate, and neutral states of citrine can be excited with relative populations that depend on pH and excitation wavelength (see below).

High-Energy Transition

Ser-65→Gly in citrine suppresses the neutral state absorption as in T203Y and T203F. However, the neutral state absorption of citrine at 412 nm is enhanced (FIG. 9A), compared with the 395 nm in T203Y and wt GFP, on external protonation by the low-pH buffer according to the FCS results. The neutral state transition in other GFP mutants (e.g., T203Y) can be probed via the blue (≈460 nm) emission tail of the main band (524 nm) and reveals a more complex relaxation pathway as multi-exponential fluorescence decays (Brejc et al., supra, 1977; Kummer et al., supra, 1998). After 405-nm excitation of citrine (pH 4.9), the emission spectrum (FIG. 9A) exhibits a broadening of the blue wing of the 524-nm band, and in the time domain, this fluorescence decays as a multi-exponential where the fitting parameters depend on the detection wavelength ($\lambda_f$; FIG. 12). The ultrafast time constant (≈40 ps) is attributed to the neutral state $S^N_0 \rightarrow S^N_1$ transition with an efficient nonradiative pathway because of the excited-state proton transfer (≈10–150 ps) observed in 405-nm excited GFP mutants, or possibly photoisomerization. The second component (400–800 ps), with an amplitude ratio that increases with $\lambda_f$ (460–560 nm), is likely to represent the relatively nonradiative intermediate state $SI_0 \rightarrow S^I_1$ relaxation. In citrine at low pH, the third decay component ($\tau_{f3} \approx 3.3$ ns) is slightly faster than the $S^A_1$-state lifetime (3.61 ns), indicating that the barrier height between the $S^A_1$ and $S^I_1$ state is reduced in low pH environment, facilitating barrier crossing. These comparative excited-state dynamics as a function of the excitation energy suggest that the fluorescence quantum yield depends on $\lambda_{ex}$.

Over the pH range 4.9–9.0, dsRed does not absorb significantly around 395 nm, but the residual absorption around that wavelength is slightly above the baseline (FIG. 9). The fluorescence detected at $\lambda_f \geq 583$ nm builds up for a few picoseconds (ps; 34+/−10 ps), when dsRed is excited at 405 nm, before decaying at a rate (3.68 ns)$^{-1}$ similar to the anionic state fluorescence. Furthermore, the fluorescence detected at 560-nm decays as a biexponential with a fast (412+/−49 ps) component of small amplitude ratio (≈0.13). These features can be attributed to a minor neutral state transition in the dsRed chromophore followed by excited-state proton transfer to the anionic state before fluorescing. The light-driven flicker observed by FCS in dsRed supports this argument. It is also possible that a small residue of immature green species acts as a donor in fluorescence resonance energy transfer pair with mature dsRed.

Molecular Hydrodynamics and Protein Configurations

The fluorescence intensity of weakly illuminated fluorophore increases linearly with laser intensity with a constant molecular diffusion time ($\tau_D$) in these FCS studies. The three-dimensional-lateral diffusion coefficient (D) of dsRed (2.6+/−0.2×10$^{-11}$ m$^2$s$^{-1}$) is slow compared with (4.0+/−0.2)×10$^{-11}$ m$^2$s$^{-1}$ for citrine (pH 9.0), as measured relative to rhodamine green (D≈2.8×10$^{-10}$ m$^2$s$^{-1}$; Meseth et al., *Biophys. J.* 76:1619–1631 (1999)). The Stokes-Einstein equation, D=$K_B$T/6παη, relates D and the effective hydrodynamic radius (a), where $K_B$, T, and η are the Boltzmann constant, temperature (300 K), and viscosity (η≈1×10$^{-3}$ kgm$^{-1}$s$^{-1}$), respectively. The hydrodynamic radius of dsRed (8.1+/−0.3 nm) is approximately 1.5 times larger than that of citrine (3.9+/−0.2 nm). For a spherical shape, this implies an effective volume 3.6+/−0.2 times larger.

Figure 14:
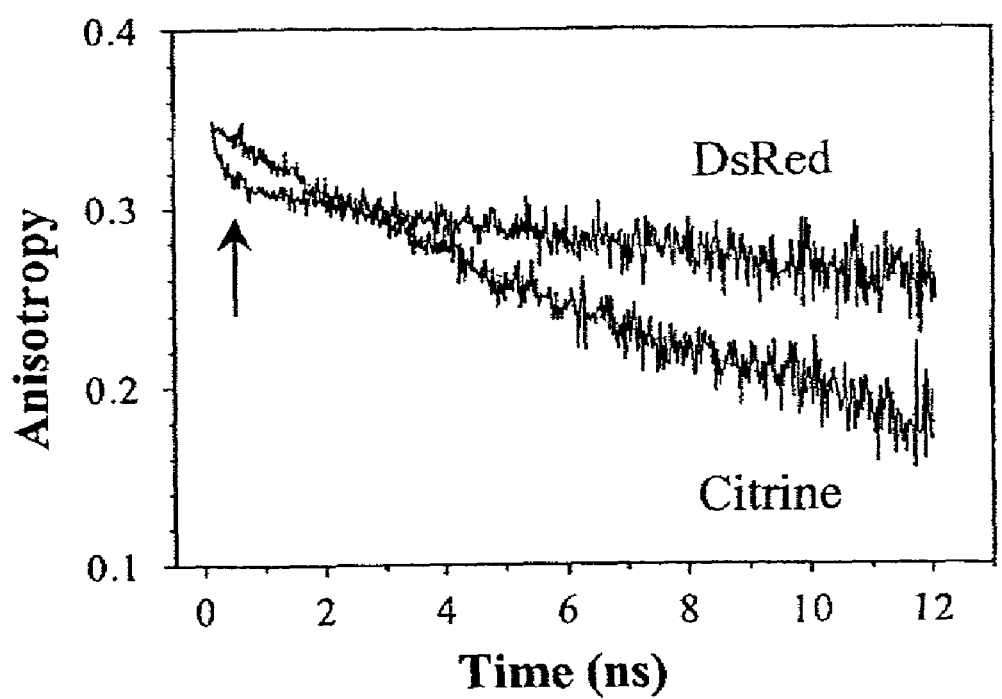
FIG. 14 shows the time-resolved fluorescence anisotropy of dsRed and citrine (pH 9.0) by using TCSPC. The anisotropy of 490-nm excited citrine decays as a single exponential with rotational time $\phi$=16+/−2 ns. To the contrary, dsRed anisotropy decays as a biexponential under the same experimental conditions, with a fast $\phi_f$=211 ps (indicated by ↑) and a slow $\phi_S$=53 6 8 ns rotational time with fast-to-slow amplitude ratio of ≈0.13.

For further comparison, the rotational correlation time (φ) of the excited-state dipole moments in dsRed and citrine were measured by using time-resolved fluorescence anisotropy. The anisotropy of citrine decays as a single exponential with a rotational correlation time $\phi_C$=16+/−2 ns (FIG. 14), which is independent of $\lambda_{ex}$ and pH within the experimental uncertainty. These results agree with the rotational correlation time (≈16 ns) of wt GFP and S65T (24). The fluorescence anisotropy of dsRed reveals a quite different behavior through a biexponential decay including a fast ($\phi_F$=211+/−6 ps) and a slow ($\phi_S$=53+/−8 ns) rotational time, that is ≈3.3+/−0.6 times slower than citrine, implying a larger effective hydrodynamics volume for dsRed. The slower rotational time in dsRed increased with buffer viscosity (by adding glycerol) whereas the faster rotational time was not affected. Although rotational times that are significantly longer than the excited-state fluorescence lifetimes are difficult to measure accurately, these results were reproducible with the stated precision. The effective volume (V) of a molecule can be determined from the rotational diffusion time, V=$K_B$Tφ/η, assuming a spherical shape. For dsRed, the volume V=220+/−30 nm$^3$ compared with 66+/−8 nm$^3$ for citrine implies an effective volume for dsRed that is 3.4+/−0.6 times larger than citrine.

Both translational and rotational diffusion experiments suggest that dsRed exists in an oligomer configuration even at ≈10$^{-9}$ and 10$^{-6}$ M used in the FCS and TCSPC experiments, respectively. On the basis of FCS results at ≈1 nM, an upper bound for the dissociation constant is ≦$10^{-9}$ M. Baird et al. postulate that dsRed is an oligomer (tetramer) in its most stable configuration (supra, 2000). Within experimental uncertainty, our estimated rotational time (i.e., protein volume) agrees with the tetramer hypothesis of dsRed configuration.

The single-exponential decay of the citrine anisotropy, at a rate consistent with expected hydrodynamic volume, and a steady-state initial anisotropy ($r_0$=0.39+/−0.01), suggests immobility of the chromophore inside its β barrel. However, the dsRed chromophore seems to undergo internal depolarization on an ≈211 ps time scale, whereas the overall rotational motion of the protein occurs with an ≈53 ns period. The steady-state anisotropy ($r_0$=0.30+/−0.02) and internal depolarization of dsRed are consistent with an energy transfer between nonparallel transition dipoles of neighboring chromophores forming individual oligomers. Rocking of a less constricted chromophore undergoing internal rotation within its polypeptide shell and/or relative to adjacent units of the oligomer are also possibilities. Both are consistent with the absence of viscosity effects on the depolarization rate. The steady-state an-isotropy of dsRed and citrine in pH 9 are within the uncertainty range of time-resolved initial anisotropy. The depolarization angle between the absorbing and emitting dipole moment in dsRed is 24+/−3° compared with 5+/−5° in citrine as estimated from the steady-state anisotropy.

Photobleaching and Denaturation Recovery

In molecular studies by using FCS in solution, as the illumination intensity approaches the saturation threshold, the apparent diffusion time starts decreasing because of photobleaching, and the triplet state population builds up sufficiently to be recognized. The intensity-dependent measurements allow us to characterize the photobleaching quantum yield ($\Phi_b$) by monitoring the variation of the apparent diffusion time with excitation rate. The slope of the apparent diffusion rate constant (1/$\tau_D$) vs. excitation rate ($k_{ex}$) gives directly the $\Phi_b$ values. Because of the triplet state population, flicker dynamics and possibly photobleaching, the apparent saturation threshold in dsRed ($I_{Sat}$≈30 kWcm$^{-2}$≡7.8+/−$10^{22}$ photon/cm$^{-2}$ s$^{-1}$, or $k_{ex}$≈1×$10^7$ s$^{-1}$) is more than an order of magnitude lower than predicted from the fluorescence decay time ($I_{Sat}$=($\sigma \tau_f$)$^{-1}$≈2.2×$10^{24}$ photon/cm$^{-2}$ s$^{-1}$) of a two-level system with excitation cross section s at 514 nm. The estimated $\Phi_b$ of dsRed is ≈9.5 3×$10^{-6}$ in pH 9.0 for 514-nm excitation compared with ≈2.6×$10^{-5}$ for citrine under 488 nm illumination, which suggests that the fluorophore can emit ≈$10^5$ photons before photobleaching. These values are in agreement with the estimated $\Phi_b$ for EGFP in a gel at pH 8 (Peterman et al., *J. Phys. Chem. A* 103:10553–10560 (1999)) by using wide-field microscopy. Baird et al. (supra, 2000) reported a smaller photobleaching yield that might be caused by the different illumination wavelength and intensity. The fluorescence signal of dsRed at pH 3.5 was indistinguishable from the background signal of pure buffer. However, 30% of the dsRed fluorescence was recovered by raising the pH to 6.6 after 5 min.

In summary, the molecular dynamics of a red fluorescent protein (dsRed) from coral and a newly designed YFP mutant (citrine) have been investigated (on a $10^{-6}$ to $10^{-11}$ sec time scale) by using FCS and TCSPC. Citrine exhibits external proton binding (pKa≈5.7) kinetics on the tens-of-microseconds time scale. In dsRed, proton-binding kinetics are insignificant over the pH range 3.9–9.0, so its fluorescence yield is pH insensitive, unique among bright GFPs. Light-driven photo-conversions occur on a 600+/−400-ms time scale with a quantum yield ≈$10^{-3}$ at high pH and are conspicuous in FCS measurements on dsRed, citrine, and other GFPs.

The most stable configuration of dsRed as expressed in *E. coli* is probably a tetramer, in the concentration range ≈$10^{-6}$ M, which implies an oligomer dissociation constant ≦$10^{-9}$ M. The biexponential anisotropy decay reveals a fast (≈211 ps) depolarization of dsRed fluorescence, which is attributed to energy transfer among nonparallel chromophores forming the oligomer and possibly involving internal motion of the chromophore. However, expression of a dsRed construct with amyloid precursor protein in mammalian neurons yields monomers that provide convenient fluorescence resonance energy transfer with a GFP, suggesting that the tetramerization need not be a problem in cellular applications.

The bright first-excited anionic state of dsRed has a long lifetime of 3.65 ns, independent of pH, and citrine has a lifetime of 3.61 ns. Citrine, however, also shows an additional short (880 ps) fluorescence decay component (≈26%) at low pH because of the intermediate state. As in most GFP mutants, the virtually dark neutral excited state of citrine at low pH exhibits a complex fluorescence relaxation with efficient nonradiative pathways, as revealed by multi-exponential fluorescence decays on the picosecond-to-nanosecond time scales.

DsRed and citrine both possess a large two-photon excitation cross section and, therefore, are excellent fluorescent markers for biological research by using multiphoton fluorescence microscopy.

Although the invention has been described with reference to the above example, it will be understood that modifications and variations are encompassed within the spirit and scope of the invention. Accordingly, the invention is limited only by the following claims.

The invention claimed is:

1. An isolated polypeptide comprising a circularly permuted *Aequorea*-related fluorescent protein moiety comprising:
    a linker moiety linking the amino-terminal and carboxy-terminal amino acids of a fluorescent protein, wherein the amino and carboxy termini are linked as internal amino acids in the circularly permuted *Aequorea*-related fluorescent protein moiety; and
    two terminal ends, wherein the first end is an amino-terminal end and the second end is a carboxy terminal end and wherein the amino and carboxy terminal ends of the circularly permuted *Aequorea*-related fluorescent protein moiety are different from the amino-terminal and carboxy-terminal amino acids of the fluorescent protein,
    wherein the amino acid residues of said fluorescent protein are numbered in conformance with native *Aquorea* green fluorescent protein (SEQ ID NO: 3) and wherein the first serine residue following methionine-1 in said fluorescent protein is designated amino acid residue 2, and wherein the amino-terminal end of the circularly permuted *Aequorea*-related fluorescent protein moiety is selected from the group consisting of E142, Y143, Y145, H148, D155, H169, E172, D173, A227 and I229, and the carboxy-terminal end of the circularly permuted *Aequorea*-related fluorescent protein moiety is selected from the group consisting of N144, N146, N149, K162, K156, N170, I171, D173, E172, A227, and I229, and
    wherein said circularly permuted fluorescent protein moiety comprises an optically active polypeptide capable of emitting light.

2. The polypeptide of claim 1, wherein the *Aequorea*-related fluorescent protein moiety is a GFP (SEQ ID NO:3), CFP, or YFP.

3. The polypeptide of claim 1, wherein the *Aequorea*-related fluorescent protein moiety is a citrine (SEQ ID NO:65).

4. The polypeptide of claim 1, wherein the linker moiety is GGTGEL (SEQ ID NO: 1), GGTGGS (SEQ ID NO:63), or FKTRHN (SEQ ID NO:2).

5. The polypeptide of claim 1, wherein said linker moiety is inserted at a site corresponding to a residue selected from residues 128–148, residues 155–160, residues 168–176 or residues 227–229 of the fluorescent protein.

6. The polypeptide of claim 1, wherein the amino-terminal end of the circularly permuted *Aequorea*-related fluorescent protein moiety is Y145 and the carboxy-terminal end of the circularly permuted *Aequorea*-related fluorescent protein moiety is selected from the group consisting of N144, N146, N149, K162, K156, N170, I171, D173, E172, A227, and I229, of the fluorescent protein, respectively.

7. The polypeptide of claim 1, further comprising a sensor polypeptide wherein the sensor polypeptide is calmodulin, a zif zinc finger domain, or citrine.

8. The polypeptide of claim 7, wherein the sensor polypeptide is a zif zinc-finger domain.

9. The polypeptide of claim 7, wherein the sensor polypeptide is calmodulin.

10. The polypeptide of claim 7, wherein the sensor polypeptide is selected from the group consisting of a calmodulin-binding domain of skMLCKp, smMLCK, CaMKII, Caldesmon, and Calspermin.

11. The polypeptide of claim 1, wherein the circularly permuted *Aequorea*-related fluorescent protein further comprises a localization sequence.

12. A circularly permuted *Aequorea*-related fluorescent protein moiety comprising:
    a linker moiety linking the amino-terminal and carboxy-terminal amino acids of citrine (SEQ ID NO:65), wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein, wherein the amino acid residues of said citrine (SEQ ID NO: 65) are numbered in conformance with native *Aquorea* green fluorescent protein (SEQ ID NO: 3) and wherein the first serine residue following methionine-1 in said fluorescent protein is designated amino acid residue 2, and wherein the amino-terminal end of the circularly permuted *Aequorea*-related fluorescent protein moiety is selected from the group consisting of E142, Y143, Y145, H148, D155, H169, E172, D173, A227 and I229, and the carboxy-terminal end of the circularly permuted *Aequorea*-related fluorescent protein moiety is selected from the group consisting of N144, N146, N149, K162, K156, N170, I171, D173, E172, A227, and I229, wherein said circularly permuted fluorescent protein moiety comprises an optically active polypeptide capable of emitting light; and a sensor polypeptide which is responsive to a chemical, biological, electrical or physiological parameter.

13. A circularly permuted fluorescent protein encoded by a nucleic acid sequence produced by the method of producing a circularly permuted-fluorescent-protein-encoding nucleic acid sequence comprising:

linking a nucleic acid sequence encoding a linker moiety to the 5' nucleotide of a polynucleotide encoding a circularly-permuted *Aequorea*-related fluorescent protein moiety of claim 12;

circularizing the polynucleotide with the nucleic acid sequence encoding the linker sequence; and cleaving the circularized polynucleotide with a nuclease, wherein cleavage linearizes the circularized polynucleotide.

* * * * *